United States Patent
Khademhosseini et al.

(10) Patent No.: US 11,058,800 B2
(45) Date of Patent: Jul. 13, 2021

(54) BIOADHESIVE FOR CORNEAL REPAIR

(71) Applicants: THE BRIGHAM AND WOMEN'S HOSPITAL, INC., Boston, MA (US); MASSACHUSETTS EYE AND EAR INFIRMARY, Boston, MA (US)

(72) Inventors: Ali Khademhosseini, Cambridge, MA (US); Nasim Annabi, Cambridge, MA (US); Reza Dana, Newton, MA (US); Ahmad Kheirkhah, Boston, MA (US)

(73) Assignees: Massachusetts Eye and Ear Infirmary, Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 16/070,643

(22) PCT Filed: Feb. 8, 2017

(86) PCT No.: PCT/US2017/016917
§ 371 (c)(1),
(2) Date: Jul. 17, 2018

(87) PCT Pub. No.: WO2017/139318
PCT Pub. Date: Aug. 17, 2017

(65) Prior Publication Data
US 2019/0022280 A1    Jan. 24, 2019

Related U.S. Application Data

(60) Provisional application No. 62/292,752, filed on Feb. 8, 2016.

(51) Int. Cl.
*A61L 27/38* (2006.01)
*A61L 27/22* (2006.01)
*A61L 27/52* (2006.01)
*A61P 27/02* (2006.01)

(52) U.S. Cl.
CPC ......... *A61L 27/3804* (2013.01); *A61L 27/222* (2013.01); *A61L 27/3839* (2013.01); *A61L 27/52* (2013.01); *A61P 27/02* (2018.01); *A61L 2430/16* (2013.01)

(58) Field of Classification Search
CPC ............... A61L 2430/16; A61L 27/222; A61L 27/3804; A61L 27/3839; A61L 27/52; A61P 27/02
See application file for complete search history.

(56) References Cited

U.S. PATENT DOCUMENTS

| | | |
|---|---|---|
| 5,064,430 A | 11/1991 | Urry |
| 5,674,623 A | 10/1997 | Haddon et al. |
| 6,458,386 B1 | 10/2002 | Schacht et al. |
| 6,585,873 B1 | 7/2003 | Solomon et al. |
| 6,608,040 B1 | 8/2003 | Lin et al. |
| 7,435,425 B2 | 10/2008 | Qian et al. |
| 7,547,446 B2 | 6/2009 | Qian et al. |
| 7,854,923 B2 | 12/2010 | Chen et al. |
| 7,871,637 B2 | 1/2011 | Qian et al. |
| 7,871,639 B2 | 1/2011 | Schankereli et al. |
| 8,092,820 B2 | 1/2012 | Qian et al. |
| 8,314,218 B2 | 11/2012 | Fallus et al. |
| 8,383,141 B2 | 2/2013 | Qian et al. |
| 8,513,217 B2 | 8/2013 | Chen et al. |
| 9,066,991 B2 | 6/2015 | Preiss-Bloom et al. |
| 9,084,728 B2 | 7/2015 | Goessl et al. |
| 2004/0110439 A1 | 6/2004 | Chaikof et al. |
| 2005/0112182 A1 | 5/2005 | Minami et al. |
| 2008/0312156 A1 | 12/2008 | Setton et al. |
| 2009/0175946 A1 | 7/2009 | Gaissmaier et al. |
| 2012/0128653 A1 | 5/2012 | Goessl et al. |
| 2013/0172985 A1 | 7/2013 | Prestwich et al. |
| 2014/0107065 A1 | 4/2014 | Chen et al. |
| 2014/0377326 A1 | 12/2014 | Niu et al. |
| 2015/0037314 A1 | 2/2015 | Larsen |
| 2015/0209109 A1 | 7/2015 | Rege et al. |
| 2015/0291939 A1 | 10/2015 | Tomer et al. |

FOREIGN PATENT DOCUMENTS

| | | |
|---|---|---|
| JP | 2002-506431 A | 2/2002 |
| JP | 2009-522001 A | 6/2009 |
| KR | 10-1562366 | 10/2015 |
| WO | WO 98/55161 | 12/1998 |
| WO | WO 2007/079053 | 7/2007 |
| WO | WO 2016/022807 | 2/2016 |

OTHER PUBLICATIONS

Allen et al., "Prospective Randomized Study Evaluating a Biodegradable Polymeric Sealant for Sealing Intraoperative Air Leaks That Occur During Pulmonary Resection", The Annals of Thoracic Surgery 77:1792-1801 (2004).
Alleyne et al., "Efficacy and biocompatibility of a photopolymerized, synthetic, absorbable hydrogel as a dural sealant in a canine craniotomy model", Journal of Neurosurgery 88:308-313 (1998).
Anegg et al., "Efficiency of fleece-bound sealing (TachoSil®) of air leaks in lung surgery: a prospective randomised trial", European Journal of Cardio-thoracic Surgery 31:198-202 (2007).
Annabi et al., "The fabrication of elastin-based hydrogels using high pressure $CO_2$", Biomaterials 30:1-7 (2009).
Annabi et al., "Synthesis of highly porous crosslinked elastin hydrogels and their interaction with fibroblasts in vitro", Biomaterials 30:4550-4557 (2009).
Annabi et al., "Cross-linked open-pore elastic hydrogels based on tropoelastin, elastin and high pressure $CO_2$", Biomaterials 31:1655-1665 (2010).
Annabi et al., "Highly Elastic Micropatterned Hydrogel for Engineering Functional Cardiac Tissue", Advanced Functional Materials 23:4950-4959 (2013).

(Continued)

*Primary Examiner* — Sarah Pihonak
(74) *Attorney, Agent, or Firm* — Fish & Richardson P.C.

(57) ABSTRACT

The present invention provides compositions and methods for repair and reconstruction of defects and injuries to the cornea.

12 Claims, 20 Drawing Sheets

(56) References Cited

OTHER PUBLICATIONS

Annabi et al., "Engineered cell-laden human protein-based elastomer", Biomaterials 34(22):5496-5505 (2013).
Annabi et al., "25th Anniversary Article: Rational Design and Applications of Hydrogels in Regenerative Medicine", Advanced Materials 26(1):85-124 (2014).
Annabi et al., "Surgical Materials: Current Challenges and Nano-enabled Solutions", Nano Today 9(5):574-589 (2014).
Anselmo et al., "Platelet-like Nanoparticles: Mimicking Shape, Flexibility, and Surface Biology of Platelets to Target Vascular Injuries", ACS Nano 8(11):11243-11253 (2014).
Assmann et al., "The degeneration of biological cardiovascular prostheses under pro-calcific metabolic conditions in a small animal model", Biomaterials 1-13 (2014).
Baldock et al., "Shape of tropoelastin, the highly extensible protein that controls human tissue elasticity", Proceedings of the National Academy of Sciences 108(11):4322-4327 (2011).
Baranoski S., "Choosing a wound dressing, part 1", Nursing2008 60-61 (2008).
Bertassoni et al., "Hydrogel Bioprinted Microchannel Networks for Vascularization of Tissue Engineering Constructs", Lab on a Chip 14(13):2202-2211 (2014).
Betre et al., "Chondrocytic differentiation of human adipose-derived adult stem cells in elastin-like polypeptide", Biomaterials 27:91-99 (2006).
Bitton et al., "Phloroglucinol-based biomimetic adhesives for medical applications", Acta Biomaterialia 5:1582-1587 (2009).
Bottcher-Haberzeth et al., "Tissue engineering of skin", Burns 36:450-460 (2010).
Buckley et al., "Silver carbonate nanoparticles stabilised over alumina nanoneedles exhibiting potent antibacterial properties", Chemical Communications 4013-4015 (2008).
Buskens et al., "The use of a surgical sealant (CoSeal®) in cardiac and vascular reconstructive surgery: an economic analysis", The Journal of Cardiovascular Surgery 47(2):161-170 (2006).
Camci-Unal et al., "Synthesis and Characterization of Hybrid Hyaluronic Acid-Gelatin Hydrogels", Biomacromolecules 14(4):1085-1092 (2013).
Carlson et al., "Giant Papillary Conjunctivitis Associated With Cyanoacrylate Glue", American Journal of Ophthalmology 104(4):437-438 (1987).
Carrico et al., "Lithographic Patterning of Photoreactive Cell-Adhesive Proteins", Journal of the American Chemical Society 129(16):4874-4875 (2007).
Cavanaugh et al., "Infectious Keratitis and Cyanoacrylate Adhesive", American Journal of Ophthalmology 111 (4):466-472 (1991).
Cha et al., "Controlling Mechanical Properties of Cell-Laden Hydrogels by Covalent Incorporation of Graphene Oxide", Small 10(3):514-523 (2014).
Charati et al., "Hydrophilic elastomeric biomaterials based on resilin-like polypeptides", Soft Matter 5(18):3412-3416 (2009).
Ifkovits et al., "Review: Photopolymerizable and Degradable Biomaterials for Tissue Engineering Applications", Tissue Engineering 13(10):2369-2385 (2007).
Huang et al., "Generation of Synthetic Elastin-Mimetic Small Diameter Fibers and Fiber Networks", Macromolecules 33(8):2989-2997 (2000).
Chou et al., "Genetically encoding an aliphatic diazirine for protein photocrosslinking", Chemical Science 2:480-483 (2011).
Costa et al., "Stimuli-Responsive Thin Coatings Using Elastin-Like Polymers for Biomedical Applications", Advanced Functional Materials 19:3210-3218 (2009).
Deacon et al., "Antimicrobial efficacy of tobramycin polymeric nanoparticles for Pseudomonas aeruginosa infections in cystic fibrosis: formulation, characterisation and functionalisation with domase alfa (DNase)", Journal of Controlled Release (2015). (16 pages).
Debelle et al., "Elastin: molecular description and function", The International Journal of Biochemistry & Cell Biology 31:261-272 (1999).
Di Zio et al., "Mechanical Properties of Artificial Protein Matrices Engineered for Control of Cell and Tissue Behavior", Macromolecules 36(5):1553-1558 (2003).
Elvin et al., "A highly elastic tissue sealant based on photopolymerised gelatin", Biomaterials 31:8323-8331 (2010).
Elzoghby A., "Gelatin-based nanoparticles as drug and gene delivery systems: Reviewing three decades of research", Journal of Controlled Release 172:1075-1091 (2013).
Fogle et al., "Tissue Adhesive Arrests Stromal Melting in the Human Cornea", American Journal of Ophthalmology 89(6):795-802 (1980).
Foo et al., "Two-component protein-engineered physical hydrogels for cell encapsulation", Proceedings of the National Academy of Sciences 106(52):22067-22072 (2009).
Gaharwar et al., "Shear-Thinning Nanocomposite Hydrogels for the Treatment of Hemorrhage", ACS Nano 8 (10):9833-9842 (2014).
Galler et al., "Self-assembling Multidomain Peptide Hydrogels: Designed Susceptibility to Enzymatic Cleavage Allows Enhanced Cell Migration and Spreading", Journal of the American Chemical Society 132(9):3217-3223 (2010).
Giannandrea et al., "Diverse functions of matrix metalloproteinases during fibrosis", Disease Models & Mechanisms 7:193-203 (2014).
Glickman et al., "A Polymeric Sealant Inhibits Anastomotic Suture Hole Bleeding More Rapidly Than Gelfoam/ Thrombin: Results of a Randomized Controlled Trial", Archives of Surgery 137:326-331 (2002).
Gorgieva et al., "Collagen- vs. Gelatine-Based Biomaterials and Their Biocompatibility: Review and Perspectives", Biomaterials Applications for Nanomedicine, InTech (2011). (38 pages).
Hassan et al., "Smart copper oxide nanocrystals: Synthesis, characterization, electrochemical and potent antibacterial activity", Colloids Surfaces B: Biointerfaces 97:201-206 (2012).
He et al., "Polymorphisms in the Human Tropoelastin Gene Modify In Vitro Self-Assembly and Mechanical Properties of Elastin-Like Polypeptides", PLOS ONE 7(9):e46130 (2012). (12 pages).
Hida et al., "Retinal Toxicity of Cyanoacrylate Tissue Adhesive in the Rabbit", Retina 8:148-153 (1988).
Hjortnaes et al., "Directing Valvular Interstitial Cell Myofibroblast-Like Differentiation in a Hybrid Hydrogel Platform", Advanced Healthcare Materials 4:121-130 (2015).
Hrabchak et al., "Assessment of biocompatibility and initial evaluation of genipin cross-linked elastin-like polypeptides in the treatment of an osteochondral knee defect in rabbits", Acta Biomaterialia 6:2108-2115 (2010).
Wissink et al., "Immobilization of heparin to EDC/NHS-crosslinked collagen. Characterization and in vitro evaluation", Biomaterials 22:151-163 (2001).
Wolbank et al., "Non-invasive in vivo tracking of fibrin degradation by fluorescence imaging", Journal of Tissue Engineering and Regenerative Medicine 9:973-976 (2015).
Xia et al., "Tunable Self-Assembly of Genetically Engineered Silk-Elastin-Like Protein Polymers", Biomacromolecules 12(11):3844-3850 (2011).
Xia et al., "Nano-structured smart hydrogels with rapid response and high elasticity", Nature Communications 4:2226 (2013). (11 pages).
Xu et al., "Rheological Properties of Cysteine-Containing Elastin-Like Polypeptide Solutions and Hydrogels", Biomacromolecules 13(8):2315-2321 (2012).
Zhang et al., "Artificial Polypeptide Scaffold for Protein Immobilization", Journal of the American Chemical Society 127(29):10136-10137 (2005).
Zhao et al. "Photocrosslinkable Gelatin Hydrogel for Epidermal Tissue Engineering", Advanced Healthcare Materials. 5(1):108-118 (2016).
Zhou et al., "Biomimetic mineralization of anionic gelatin hydrogels: effect of degree of methacrylation", RSC Advances 4:21997-22008 (2014).
Zhu et al., "Design properties of hydrogel tissue-engineering scaffolds", Expert Review of Medical Devices 8 (5):607-626 (2011).
Yue et al. "Synthesis, properties, and biomedical applications of gelatin methacryloyl (GelMA) hydrogels." Biomaterials 73; 254-71 (2015).

(56) References Cited

OTHER PUBLICATIONS

Nichol et al., "Cell-laden microengineered gelatin methacrylate hydrogels", Biomaterials 31(21): 5536-5544 (2010).
Chen et al., "Layer-by-Layer Bioprinting of Stem Cells for Retinal Tissue Regeneration", University of California, San Diego (2016). (22 pages).
Chen et al., "Functional Human Vascular Network Generated in Photocrosslinkable Gelatin Methacrylate Hydrogels", Advanced Functional Materials 22(10):2027-2039 (2012).
International Search Report dated Apr. 21, 2017, in correspondence to International Application No. PCT/US17/16917.
Itano H., "The optimal technique for combined application of fibrin sealant and bioabsorbable felt against alveolar air leakage", European Journal of Cardio-thoracic Surgery 33:457-460 (2008).
Jun et al., "Comparison of Bursting Pressure after Scleral Tunnel Incision Sealed with Sutures or an Adherent Ocular Bandage in Human Globes", The Journal of International Medical Research 40:756-760 (2012).
Katagiri et al., "All Six Modules of the Gelatin-binding Domain of Fibronectin Are Required for Full Affinity", The Journal of Biological Chemistry 278(14):11897-11902 (2003).
Kharazifia et al., "Tough and Flexible CNT—Polymeric Hybrid Scaffolds for Engineering Cardiac Constructs", Biomaterials 35(26):7346-7354 (2014).
Kim et al., "Self-Assembly of Thermally Responsive Amphiphilic Diblock Copolypeptides into Spherical Micellar Nanoparticles", Angewandte Chemie International Edition 49:4257-4260 (2010).
Kim et al., "Biomimetic Scaffolds for Tissue Engineering", Advanced Functional Materials 22:2446-2468 (2012).
Kobayashi et al., "In Vivo Evaluation of a New Sealant Material on a Rat Lung Air Leak Model", Journal of Biomedical Materials Research (Applied Biomaterials) 58:658-665 (2001).
Lai et al., "Gelatin methacrylate/carboxybetaine methacrylate hydrogels with tunable crosslinking for controlled drug release", Journal of Materials Chemistry B 4:2304-2313 (2016).
Leahey et al., "Clinical Experience with N-butyl Cyanoacryiate (Nexacryl) Tissue Adhesive", Ophthalmology 100 (2):173-180 (1993).
Lee et al., "Hydrogels for Tissue Engineering", Chemical Reviews 101(7):1869-1879 (2001).
Li et al., "Toward a Stretchable, Elastic, and Electrically Conductive Nanocomposite: Morphology and Properties of Poly[styrene-b-(ethylene-co-butylene)-b-styrene]/Multiwalled Carbon Nanotube Composites Fabricated by High-Shear Processing", Macromolecules 42(7):2587-2593 (2009).
Lim et al., "Rapid Crosslinking of Elastin-like Polypeptides with Hydroxymethylphosphines in Aqueous Solution", Biomacromolecules 8(5):1463-1470 (2007).
Lynn et al., "Antigenicity and Immunogenicity of Collagen", Journal of Biomedical Materials Research Part B: Applied Biomaterials 71B:343-354 (2004).
Macewan et al., "Elastin-Like Polypeptides: Biomedical Applications of Tunable Biopolymers", Peptide Science 94 (1):60-77 (2010).
Macewan et al., "Applications of elastin-like polypeptides in drug delivery", Journal of Controlled Release 190:314-330 (2014).
McHale et al., "Synthesis and in Vitro Evaluation of Enzymatically Cross-Linked Elastin-Like Polypeptide Gels for Cartilaginous Tissue Repair", Tissue Engineering 11(11/12):1768-1779 (2005).
Mehdizadeh et al., "Injectable citrate-based mussel-inspired tissue bioadhesives with high wet strength for sutureless wound closure", Biomaterials 33:7972-7983 (2012).
Meyer et al., "Purification of recombinant proteins by fusion with thermally-responsive polypeptides", Nature Biotechnology 17:1112-1115 (1999).
Montanaro et al., "Cytotoxicity, blood compatibility and antimicrobial activity of two cyanoacrylate glues for surgical use", Biomaterials 22:59-66 (2001).
Munoz et al., "Gelatin hydrogels formed by orthogonal thiol-norbornene photochemistry for cell encapsulation", Biomaterials Science 2:1063-1072 (2014).

Nagapudi et al., "Photomediated Solid-State Cross-Linking of an Elastin-Mimetic Recombinant Protein Polymer", Macromolecules 35(5):1730-1737 (2002).
Nakayama et al., "Enhancement of visible light-induced gelation of photocurable gelatin by addition of polymeric amine", Journal of Photochemistry and Photobiology A: Chemistry 177:205-211 (2006).
Nan et al., "Nosocomial Infection After Lung Surgery: Incidence and Risk Factors", Chest 128(4):2647-2652 (2005).
Nettles et al., "In Situ Crosslinking Elastin-Like Polypeptide Gels for Application to Articular Cartilage Repair in a Goat Osteochondral Defect Model", Tissue Engineering Part A 14(7):1133-1140 (2008).
Nettles et al., "Applications of Elastin-like Polypeptides in Tissue Engineering", Advanced Drug Delivery Reviews 62 (15):1479-1485 (2010).
Nikkhah et al., "Directed endothelial cell morphogenesis in micropatterned gelatin methacrylate hydrogels", Biomaterials 33:9009-9018 (2012).
Okajima et al., "Kinetics of volume phase transition in poly(N-isopropylacrylamide) gels", Journal of Chemical Physics 116(20):9068-9077 (2002).
Omidian et al., "Elastic, Superporous Hydrogel Hybrids of Polyacrylamide and Sodium Alginate", Macromolecular Bioscience 6:703-710 (2006).
Papatheofanis F., "Prothrombotic Cytotoxicity of Cyanoacrylate Tissue Adhesive", Journal of Surgical Research 47(4):309-312 (1989).
Park et al., "Evaluation of Polyethylene Glycol Based Hydrogel for Tissue Sealing After Laparoscopic Partial Nephrectomy in a Porcine Model", The Journal of Urology 172:2446-2450 (2004).
Paul et al., "Injectable Graphene Oxide/Hydrogel-Based Angiogenic Gene Delivery System for Vasculogenesis and Cardiac Repair", ACS Nano 8(8):8050-8062 (2014).
Qerimi et al., "Collagen hemostat significantly reduces time to hemostasis compared with cellulose: COBBANA, a single-center, randomized trial", The American Journal of Surgery 205(6):636-641 (2013).
Raphel et al., "Photoreactive elastin-like proteins for use as versatile bioactive materials and surface coatings", Journal of Materials Chemistry 22(37):19429-19437 (2012).
Rogers et al., "Materials and Mechanics for Stretchable Electronics", Science 327:1603-1607 (2010).
Shazly et al., "Viscoelastic adhesive mechanics of aldehyde-mediated soft tissue sealants", Biomaterials 29:4584-4591 (2008).
Shin et al., "Carbon Nanotube Reinforced Hybrid Microgels as Scaffold Materials for Cell Encapsulation", ACS Nano 6 (1):362-372 (2012).
Shin et al., "Carbon-Nanotube-Embedded Hydrogel Sheets for Engineering Cardiac Constructs and Bioactuators", ACS Nano 7(3):2369-2380 (2013).
Siegal et al., "Surgical Removal of Cyanoacrylate Adhesive After Accidental Instillation in the Anterior Chamber", Ophthalmic Surgery 20(3):179-181 (1989).
Spotnitz et al., "Hemostats, sealants, and adhesives III: a new update as well as cost and regulatory considerations for components of the surgical toolbox", Transfusion 52:2243-2255 (2012).
Sun et al., "Highly stretchable and tough hydrogels", Nature 489(7414):133-136 (2012).
Tang et al., "Oxidatively Responsive Chain Extension to Entangle Engineered Protein Hydrogels", Macromolecules 47(2):791-799 (2014).
Teng et al., "Morphological analysis of leucocyte transmigration in the pleural cavity", Journal of Anatomy 203:391-404 (2003).
Tessmar et al., "Customized PEG-Derived Copolymers for Tissue-Engineering Applications", Macromolecular Bioscience 7:23-39 (2007).
Than et al., "Polyethylene Glycol Hydrogel Dural Sealant May Reduce Incisional Cerebrospinal Fluid Leak After Posterior Fossa Surgery", Operative Neurosurgery 63(ONS Suppl 1):ONS182-ONS187 (2008).
Trabbic-Carlson et al., "Swelling and Mechanical Behaviors of Chemically Cross-Linked Hydrogels of Elastin-like Polypeptides", Biomacromolecules 4(3):572-580 (2003).

(56) References Cited

OTHER PUBLICATIONS

Urry et al., "Biocompatibility of the Bioelastic Materials, Poly(GVGVP) and Its γ-Irradiation Cross-Linked Matrix: Summary of Generic Biological Test Results", Journal of Bioactive and Compatible Polymers 6:263-282 (1991).
Visser et al., "Endochondral bone formation in gelatin methacrylamide hydrogel with embedded cartilage-derived matrix particles", Biomaterials 1-9 (2014).
Wang et al., "A tough biodegradable elastomer", Nature Biotechnology 20:602-606 (2002).
Weiss et al., "The Use of Tissue Adhesive in Corneal Perforations", Ophthalmology 90(6):610-615 (1983).
Welsh et al., "Engineering the Extracellular Matrix: A Novel Approach to Polymeric Biomaterials. I. Control of the Physical Properties of Artificial Protein Matrices Designed to Support Adhesion of Vascular Endothelial Cells", Biomacromolecules 1(1)23-30 (2000).
Glassman et al., "End block design modulates the Assembly and Mechanics of Thermoresponsive, Dual-Associative Protein Hydrogels", Macromolecules 48(6): 1832-1842 (2015).
Zhang et al., "A Highly Elastic and Rapidly Crosslinkable Elastin-Like Polypeptide-Based Hydrogel for Biomedical Applications", Advanced Functional Material 25(30): 4814-4826 (2015).
EP Extended European Search Report in European Appln. No. 17750660, dated Jun. 15, 2020, 10 pages.
AU Office Action in Australian Application No. 2017217454, dated May 15, 2020, 5 pages.
JP Office Action in Japanese Application No. 2018-541314, dated Oct. 21, 2020, 31 pages (with English translation).
PCT International Preliminary Report on Patentability in International Application No. PCT/US2017/016917, dated Aug. 14, 2018, 10 pages.

2D Culture
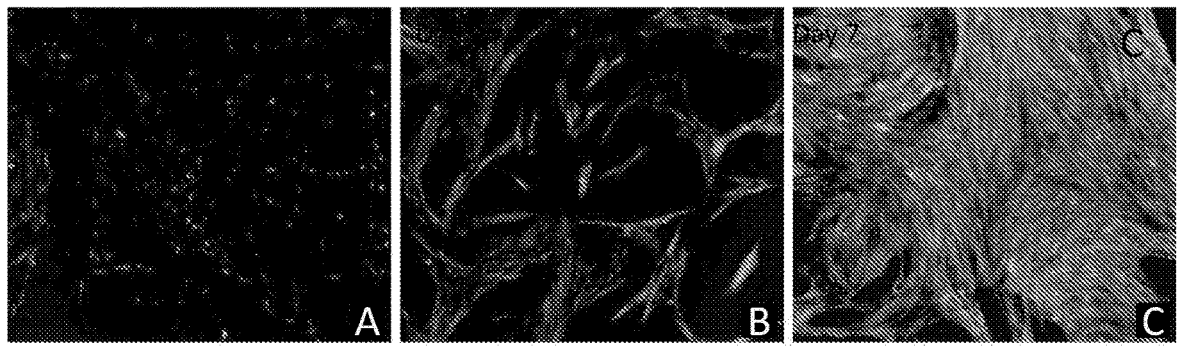
3D Culture
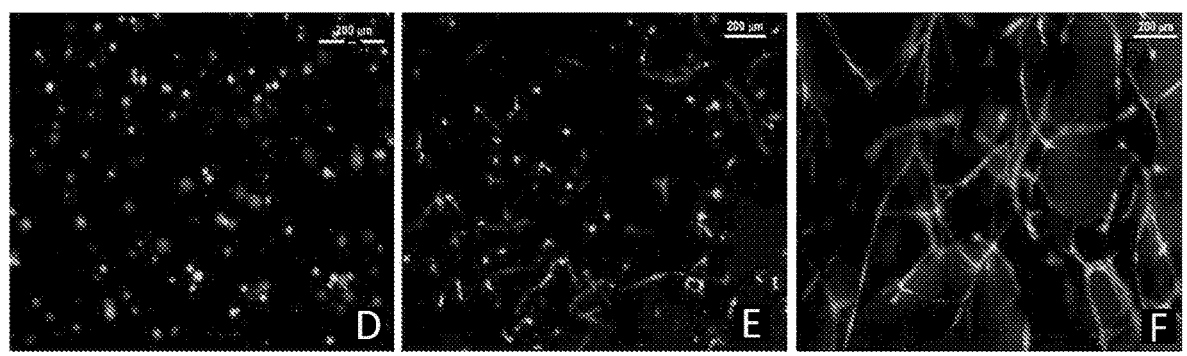
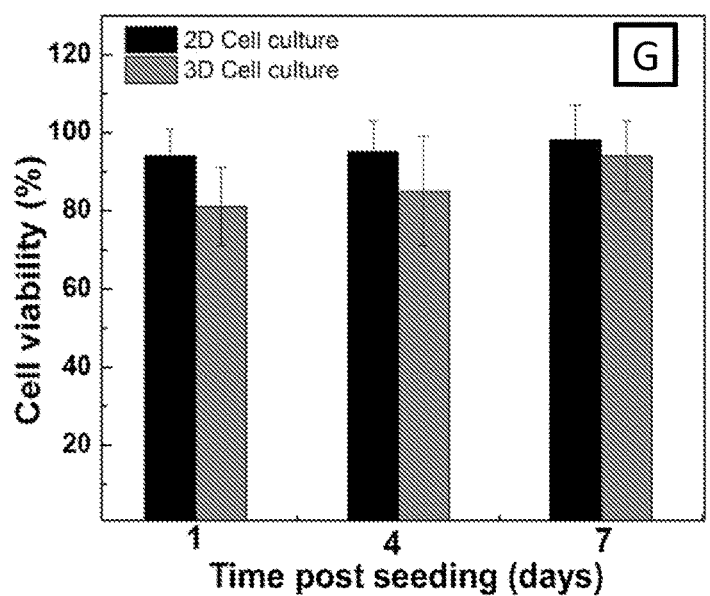
*FIG. 11A-11G*

Day 1
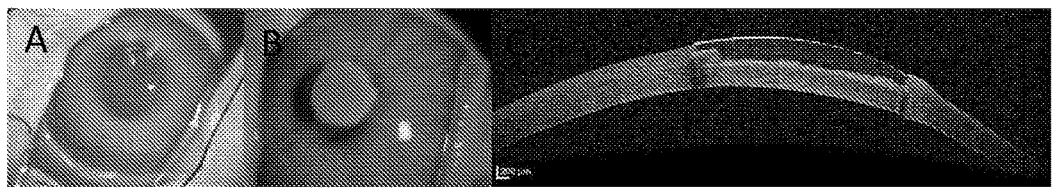
Day 7
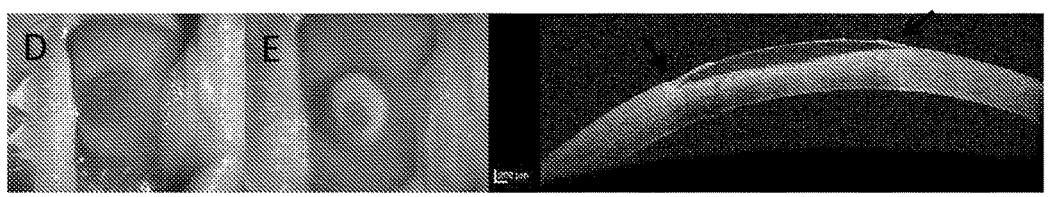
*FIG. 19A-19F*
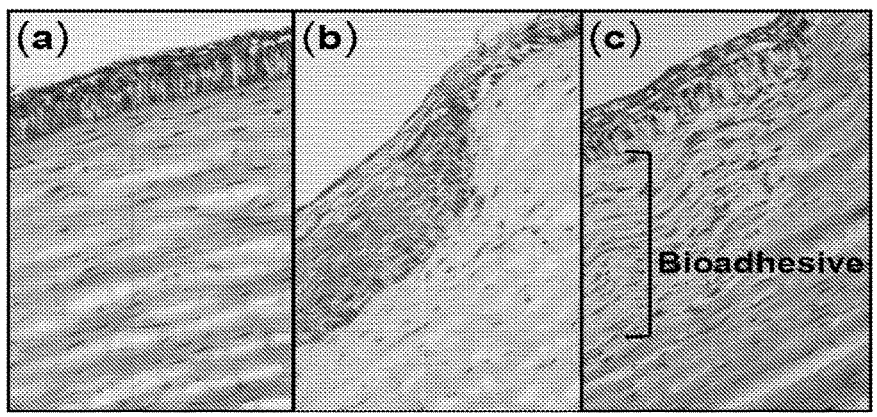
*FIG. 20A-20C*

BIOADHESIVE FOR CORNEAL REPAIR

CROSS REFERENCE TO RELATED APPLICATIONS

This application is a 371 National Phase Entry of International Patent Application No. PCT/US2017/016917 filed on Feb. 8, 2017 which claims benefit under 35 U.S.C. § 119(e) of U.S. Provisional Application No. 62/292,752 filed Feb. 8, 2016, the contents of which are incorporated herein by reference in their entirety.

FIELD OF THE DISCLOSURE

The field of the disclosure relates to improved tissue adhesives for use in repairing corneal injuries and defects. These tissue adhesives comprise elastic biopolymers which are biocompatible, biodegradable, transparent, strongly adhesive to corneal tissue, and have a smooth surface and biomechanical properties similar to the cornea.

BACKGROUND

Ocular trauma is common, accounting for nearly 5% of blindness in the general population.[1] The current standards of care for repair of corneal injuries, including lacerations, structural defects, and thinning, often require suturing, tissue/patch grafting, and/or glue application. However, these standard procedures are associated with substantial drawbacks, including: (1) corneal sutures are foreign bodies that can serve as risk factors for microbial entrapment and infection, inflammation, and neovascularization; (2) corneal sutures often induce regular or irregular astigmatism, leading to impaired visual acuity; (3) corneal transplantation and patch grafting require donor tissues, which may not be readily available; and (4) use of allogeneic tissues for grafting carries a high risk for immune reactions in acutely injured inflamed eyes. Thus, even if the structural repair is adequate with the current standards of care, the visual outcomes are often not satisfactory.[2,3] In addition, (5) application of any of the currently available glue/adhesive technologies for temporizing injured eyes until more definitive care can be offered has its own inherent limitations.

To circumvent some of the limitations of the current surgical approaches in corneal repair, the use of adhesives may be considered for fast repair of corneal injuries. However, currently there is no approved adhesive for filling corneal defects. The only approved sealant in the U.S., ReSure®, is for sealing corneal incisions of cataract surgery, and has not been designed for filling corneal defects and falls off quickly (usually in less than 3 days).[4] OcuSeal®, a sealant used in Europe, is also utilized for protecting corneal incisions but not filling corneal defects and also detaches quickly. For this reason, cyanoacrylate glue, which is approved for repair of skin wounds, is currently used as "off-label" for treating many ophthalmic settings such as corneal perforations, impending perforations and progressive corneal thinning disorders.[5,6] However, cyanoacrylate glue has several major drawbacks, including:

(1) Low biocompatibility, with cytotoxic effects on the cornea and other ocular tissues (risk of cataract formation and retinopathy if it enters the eye);[7-11] (2) lack of transparency, precluding good vision and impairing view of retrocorneal structures; (3) risk of secondary infection due to high porosity;[12] (4) difficult to control its application, with glue potentially falling off unpredictably; (5) rough surface requiring contact lens wear, which adds additional infection risk; and (6) it does not integrate with corneal tissue.

Because existing adhesives for corneal repair have major drawbacks, there is an unmet need for an adhesive for the repair and regeneration of corneal injuries that can meet the following requirements: (1) easy application; (2) biocompatible without causing any toxicity, inflammation, or neovascularization; (3) transparent so as to enable restoration of vision as quickly as possible; (4) ability to rapidly seal the corneal wound; (5) permitting corneal cells to integrate with the bioadhesive to facilitate tissue regeneration (6) biomechanical properties (rigidity and elasticity) similar to the cornea; (7) strong adhesion to corneal tissue including good stability and high retention; and (8) smooth surface to reduce the need for bandage contact lens and minimize surface area for microbial adhesion.

Photopolymerization of methacryloyl-substituted gelatin is an inexpensive and technically simple approach to fabricate hydrogels for biomedical applications.[14, 38-40] The cytocompatibility of methacryloyl-substituted gelatin has been previously proven, suggesting it has potential to be implanted into a living organism.[41-42] However, its actual function as a corneal repair material has not been evaluated yet. Moreover, the mechanical properties of methacryloyl-substituted gelatin have not been thoroughly investigated, so it is unknown if it is suitable to serve as a bioadhesive for corneal repair.

SUMMARY

Certain aspects of the present invention are directed to compositions for corneal reconstruction comprising a methacryloyl gelatin (GelMA) prepolymer, a visible light activated photoinitiator, and a pharmaceutically acceptable carrier. In some embodiments, the methacryloyl-substituted gelatin has a degree of methacryloyl substitution between 30% and 85%, between 60% and 85%, or between 70% and 80%. Methacryloyl gelatin is also referred to as methacryloyl substituted gelatin herein.

In some embodiments, the methacryloyl-substituted gelatin comprises methacrylamide substitution and methacrylate substitution, and the ratio of methacrylamide substitution to methacrylate substitution is between 80:20 and 99:1, between 90:10 and 98:2, or between 93:7 and 97:3.

In some embodiments, the methacryloyl-substituted gelatin is present at a concentration between 5% and 25% (w/v), between 17% and 55% (w/v), between 17% and 23% (w/v), between 5% and 15% (w/v), between 8% and 12% (w/v), of about 20% (w/v) or of about 10% (w/v).

In some embodiments, the visible light activated photoinitiator is selected from the group consisting of: Eosin Y, triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bis(diethylamino)benzophenone, 2-chlorothioxanthen-9-one, 4-(dimethylamino)benzophenone, phenanthrenequinone, ferrocene, diphenyl(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane (Ivocerin®), derivatives thereof, and any combination thereof.

Preferably, the visible light activated photoinitiator comprises a mixture of Eosin Y, triethanolamine, and vinyl caprolactam. In some embodiments of the photoinitiator mixture, the concentration of Eosin Y is between 0.0125 and 0.5 mM, and/or the concentration of triethanolamine is between 0.1 and 2% w/v, and/or the concentration of vinyl caprolactam is between 0.05 and 1.5% w/v.

In some embodiments of the photoinitiator mixture, the concentration of Eosin Y is between 0.025 and 0.15 mM, and/or the concentration of triethanolamine is between 0.2 and 1.6% w/v, and/or and the concentration of vinyl caprolactam is between 0.09 and 0.8% w/v. In some embodiments of the photoinitiator mixture, the concentration of Eosin Y is between 0.025 and 0.15 mM, and/or the concentration of triethanolamine is between 0.2 and 1.6% w/v, and/or the concentration of vinyl caprolactam is between 0.09 and 0.8% w/v. In some embodiments of the photoinitiator mixture, the concentration of Eosin Y is between 0.05 and 0.08 mM, and/or the concentration of triethanolamine is between 0.4 and 0.8% w/v, and/or the concentration of vinyl caprolactam is between 0.18 and 0.4% w/v. In some embodiments of the photoinitiator mixture, the concentration of Eosin Y is about 0.05 mM, and/or the concentration of triethanolamine is about 0.4% w/v, and/or the concentration of vinyl caprolactam is about 0.4% w/v. In some embodiments of the photoinitiator mixture, the concentration of Eosin Y is between 0.5 and 0.5 mM, and/or the concentration of triethanolamine is between 0.5 and 2% w/v, and/or the concentration of vinyl caprolactam is between 0.5 and 1.5% w/v. In some embodiments of the photoinitiator mixture, the concentration of Eosin Y is about 0.1 mM, the concentration of triethanolamine is about 0.5% w/v, and the concentration of vinyl caprolactam is about 0.5% w/v.

In some embodiments, the composition further comprises corneal cells. Exemplary, corneal cells include, but are not limited to, epithelial cells, endothelial cells, keratocytes, and any combinations thereof.

In some embodiments, the composition further comprises a therapeutic agent. Exemplary therapeutic agents for inclusion in the compositions include, but are not limited to, an antibacterial, an anti-fungal, an anti-viral, an anti-acanthamoebal, an anti-inflammatory, an immunosuppressive, an anti-glaucoma, an anti-VEGF, a growth factor, or any combination thereof.

Certain aspects of the present invention are directed to compositions for corneal reconstruction comprising a cross-linked methacryloyl-substituted gelatin hydrogel and a pharmaceutically acceptable carrier, wherein the crosslinked methacryloyl-substituted gelatin hydrogel has a degree of methacryloyl substitution between 30% and 85% and a concentration between 5% and 25% (w/v) in the pharmaceutically acceptable carrier. These compositions are also referred to as cross-linked compositions herein. Further, such compositions are also referred to as Gel-CORE herein.

In some embodiments, the crosslinked methacryloyl-substituted gelatin hydrogel has a degree of methacryloyl substitution between 60% and 85% and a concentration between 8% and 12% (w/v), or a degree of methacryloyl substitution between 70% and 80% and a concentration of about 10% (w/v). In some embodiments, the crosslinked methacryloyl-substituted gelatin hydrogel has a degree of methacryloyl substitution between 60% and 85% and a concentration between 17% and 25% (w/v), or a degree of methacryloyl substitution between 70% and 80% and a concentration of about 20% (w/v).

In some embodiments, the cross-linked composition has a Young's Modulus of 190-260 kPa. In some embodiments, the cross-linked composition has a Young's Modulus of 110-140 kPa.

In some embodiments, the cross-linked composition has an elastic modulus of 5-50 kPa.

In some embodiments, the cross-linked composition has a compressive modulus of 5-320 kPa. In some embodiments, the composition has a compressive modulus of 5-160 kPa. In still some other embodiments, the composition has a compressive modulus of 125-175 kPa.

In some embodiments, the cross-linked composition has wound closure strength of ≥40 kPa.

In some embodiments, the cross-linked composition has a shear resistance strength of ≥10 kPa. In some embodiments, the cross-linked composition has a shear resistance strength of ≥100 kPa.

In some embodiments, the cross-linked composition has a burst pressure of ≥15 kPa.

In some embodiments, the cross-linked composition further comprises a therapeutic agent. Some exemplary therapeutic agents are an antibacterial, an anti-fungal, an anti-viral, an anti-acanthamoebal, an anti-inflammatory, an immunosuppressive, an anti-glaucoma, an anti-VEGF, a growth factor, or any combination thereof.

In some embodiments, the cross-linked composition further comprises corneal cells. Preferred corneal cells include endothelial cells, keratocytes, or a combination thereof.

In some embodiments, the cross-linked composition is substantially transparent.

In some embodiments, the cross-linked composition has a substantially smooth surface.

Certain aspects of the present invention are directed to methods for corneal reconstruction, comprising the steps of: applying a composition comprising a methacryloyl-substituted gelatin, a visible light activated photoinitiator, and a pharmaceutically acceptable carrier to a corneal defect; and exposing the composition to visible light. In some embodiments of the method, the methacryloyl-substituted gelatin has a degree of methacryloyl substitution between 30% and 85%, between 60% and 85%, or between 70% and 80%.

In some embodiments of the method, the methacryloyl-substituted gelatin comprises methacrylamide substitution and methacrylate substitution, and the ratio of methacrylamide substitution to methacrylate substitution is between 80:20 and 99:1, between 90:10 and 98:2, or between 92:8 and 97:3.

In some embodiments of the method, the methacryloyl-substituted gelatin is present at a concentration between 5% and 25% (w/v), between 17% and 55% (w/v), between 17% and 23% (w/v), between 5% and 15% (w/v), between 8% and 12% (w/v), of about 20% (w/v) or of about 10% (w/v).

In some embodiments of the method, the visible light activated photoinitiator is selected from the group consisting of: Eosin Y, triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bis(diethylamino) benzophenone, 2-chlorothioxanthen-9-one, 4-(dimethylamino)benzophenone, phenanthrenequinone, ferrocene, diphenyl(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane (Ivocerin®), derivatives thereof, and any combination thereof.

In some embodiments of the method, the visible light activated photoinitiator comprises a mixture of Eosin Y, triethanolamine, and vinyl caprolactam. In some embodiments of the photoinitiator mixture, the concentration of Eosin Y is between 0.0125 and 0.5 mM, and/or the concentration of triethanolamine is between 0.1 and 2% (w/v), and/or the concentration of vinyl caprolactam is between 0.05 and 1.5% (w/v). In some embodiments of the method, the concentration of Eosin Y is between 0.025 and 0.15 mM, and/or the concentration of triethanolamine is between 0.2 and 1.6% (w/v), and/or and the concentration of vinyl caprolactam is between 0.09 and 0.8% w/v. In some embodiments of the method, the concentration of Eosin Y is between 0.025 and 0.15 mM, and/or the concentration of triethanolamine is between 0.2 and 1.6% w/v, and/or the concentration of vinyl caprolactam is between 0.09 and 0.8% (w/v). In some embodiments of the method, the concentration of Eosin Y is between 0.05 and 0.08 mM, and/or the concentration of triethanolamine is between 0.4 and 0.8% w/v, and/or the concentration of vinyl caprolactam is between 0.18 and 0.4% (w/v). In some embodiments of the method, the concentration of Eosin Y is about 0.05 mM, and/or the concentration of triethanolamine is about 0.4% (w/v), and/or the concentration of vinyl caprolactam is about 0.4% (w/v). In some embodiments of the method, the concentration of Eosin Y is between 0.5 and 0.5 mM, and/or the concentration of triethanolamine is between 0.5 and 2% (w/v), and/or the concentration of vinyl caprolactam is between 0.5 and 1.5% (w/v). In some embodiments of the method, the concentration of Eosin Y is about 0.1 mM, the concentration of triethanolamine is about 0.5% (w/v), and the concentration of vinyl caprolactam is about 0.5% (w/v).

Generally, a light of any suitable wavelength can be used in the method of the invention. For example, the composition can be exposed to visible light with a wavelength in the range of 450 to 550 nm. Further, exposure to light can be for any desired duration of time. For example, the composition can be exposed to visible light for a time period between 10 and 300 seconds. In some embodiments, the composition can be exposed to visible light for a time period between 20 and 120 seconds, or between 30 and 60 seconds. In some embodiments, the composition can be exposed to visible light for a time period between 60 seconds and 240 seconds. In some embodiments, the composition can be exposed to visible light for a time period of about 60 seconds, about 120 seconds, about 180 seconds or about 240 seconds. In some preferred embodiments, the composition can be exposed to visible light for a time period of about 240 seconds.

In some embodiments of the method, the composition further comprises a therapeutic agent, preferably an antibacterial, an anti-fungal, an anti-viral, an anti-acanthamoebal, an anti-inflammatory, an immunosuppressive, an anti-glaucoma, an anti-VEGF, a growth factor, or any combination thereof. In some embodiments, the composition further comprises corneal cells, preferably epithelial cells, endothelial cells, keratocytes, or a combination thereof. In some embodiments, the composition is substantially transparent. In some embodiments, the method does not comprise suturing the cornea.

In some embodiments of the method, the composition is a composition for corneal reconstruction described herein.

BRIEF DESCRIPTION OF THE DRAWINGS

FIG. 3A is a schematic diagram showing reactions used for the analysis of methacrylate groups. Step (i) shows that methacrylate groups in GelMA react with hydroxylamine under basic conditions to generate N-hydroxymethacrylamide in equal molar amount. Step (ii) shows that N-hydroxymethacrylamide forms a colored complex with Fe(III) ion under acidic conditions. FIG. 3B shows photographs of an Fe(III) solution before and after the addition of acetohydroxamic acid. The color change indicates the formation of the Fe(III)-acetohydroxamic acid complex. FIG. 3C shows normalized UV-Vis absorption spectrum of the Fe(III)-acetohydroxamic acid complex (FeAHA). The absorption peak is centered at 500 nm. FIG. 3D shows a working curve between absorbance and FeAHA concentration from a series of standard FeAHA solutions. FIG. 3E shows calculated amounts of methacrylamide and methacrylate groups in GelMA samples. The ultra-GelMA, high-GelMA, medium-GelMA, and low-GelMA refer to samples prepared with 20% (v/v), 8% (v/v), 5% (v/v), and 0.5% (v/v) MA in the reaction, respectively.

FIG. 4A is a schematic illustration of the radical generation reactions initiated by photo-induced activation of Eosin-Y, which is assisted by TEA. FIG. 4B shows UV-Vis spectra of Eosin-Y at pH 7.4 in aqueous solution. FIG. 4C shows visualization of the color change upon visible light exposure during the hydrogel formation indicating activated state of Eosin-Y.

FIGS. 11A-11G show in vitro evaluation of GelMA cytocompatiblity and spreading using corneal keratocyte cells. FIGS. 11A-11C show representative live/dead images from keratocytes attached on the surface of the Gel-CORE on days 1 (FIG. 11A), 3 (FIG. 11B) and 7 (FIG. 11C). FIGS. 11D-11F show representative images from F-actin/DAPI stained GEL-CORE containing keratocytes days 1 (FIG. 11D), 3 (FIG. 11E) and 7 (FIG. 11F) after encapsulation FIG. 11G shows quantification of cell viability on GEL-CORE over 7 days of culture.

FIG. 14A is a line graph showing representative tensile strain/stress curves, FIG. 14B is a bar graph showing tensile modulus for GelMA hydrogels produced at various light exposure times and GelMA concentrations. FIG. 14C is a bar graph showing strength at break for GelMA hydrogels, crosslinked by using various visible light exposure times and GelMA concentrations.

FIG. 15A is a line graph showing representative comressive strain/stress curves.

FIG. 15B is a bar graph showing compression modulus for GelMA hydrogels produced at various light exposure times and GelMA concentrations.

FIG. 16A is a schematic showing burst pressure setup for measuring the leaking pressure of the explanted rabbit cornea with an incisional perforation of 2 mm in diameter, after the bioadhesive was applied and photocrosslinked. Tuning the visible light exposure time (i.e., 1, 2 and 4 min.) generates hydrogels with varying burst pressure (FIG. 16B). The concentration of GelMA was 20% (w/v).

FIGS. 19A-19F are images showing in vivo application of the bioadhesive to corneal defects in rabbits. One day after application, the bioadhesive was transparent with a smooth surface without any corneal inflammation (FIG. 19A). There was an epithelial defect over the bioadhesive (FIG. 19B) and AS-OCT showed complete adhesion of the implant to the cornea (FIG. 19C). One week after the application, the bioadhesive was still transparent with no associated stromal infiltrate based on slit lamp exam (FIG. 19D). Epithelial migration over the bioadhesive was evident in fluorescein staining (FIG. 19E) as well as in AS-OCT (arrows, FIG. 19F), which also showed no gap between the bioadhesive and the stroma.

FIGS. 20A-20C are representative H&E histopathology images (200×) from rabbit corneas 2 weeks after creating a 50%-depth stromal defect (FIG. 20A, normal uninjured cornea). When a corneal defect is left to heal without bioadhesive, significant epithelial hyperplasia filling the stromal defect was observed (FIG. 20B). In contrast, when the stromal defect is filled with GelMA bioadhesive, the biomaterial is covered by epithelial cells and is retained by the cornea, filling the entire defect (FIG. 20C).

DETAILED DESCRIPTION

Figures 1A, 1B, 1C, 1D, 1E:
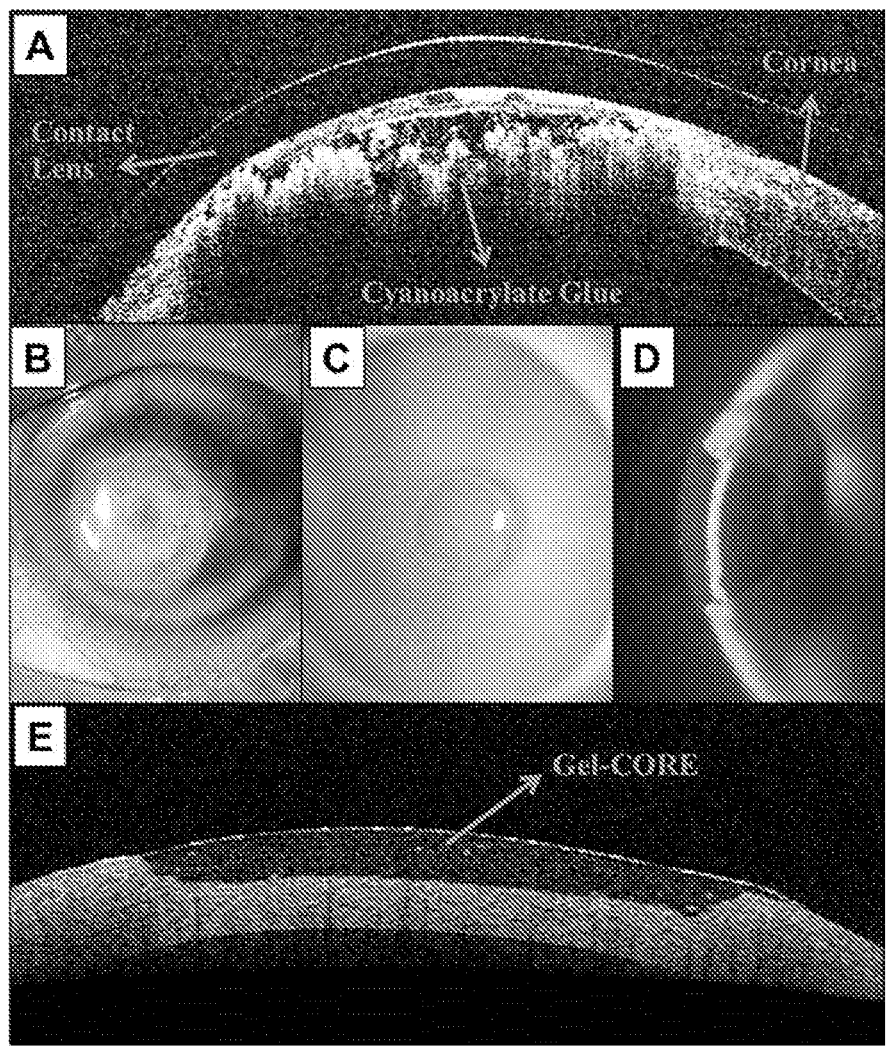
FIG. 1A is an Optical Coherence Tomography (OCT) image of cyanoacrylate glue on a patient's cornea showing its rough surface and high porosity.
FIG. 1B is a slit lamp photograph of cyanoacrylate glue showing its opaqueness.
FIGS. 1C-1D are Gel-CORE slit lamp photos and FIG. 1E is an OCT image after ex vivo application to rabbit corneal defect showing its clarity, and smoothness.

The inventors have developed and optimized specific formulations of a bioadhesive hydrogel for corneal applications: methacryloyl gelatin (GelMA) hydrogel for Corneal Reconstruction (hereafter referred to as Gel-CORE). To form Gel-CORE, a natural polymer was used, gelatin, which is derived from hydrolyzed collagen, maintaining similar bioactivity as collagen. Gelatin was chemically functionalized with methacryloyl groups to form a light activated and adhesive hydrogel, GelMA, with tunable physical properties. This hydrogel can be applied to the cornea and photopolymerized with visible light in a few seconds to form a highly adhesive hydrogel. Specific formulations were developed with desired bioadhesiveness, bioactivity and degradation profiles suitable for corneal applications.

Although widespread in biomedical applications, UV light crosslinking has potential biosafety concerns as it may lead to undesired DNA damage and ocular toxicity. GelMA comprises modified natural extracellular matrix components that can be crosslinked via visible light exposure to create an elastic and biodegradable hydrogel for corneal reconstruction and repair (Gel-CORE). Natural extracellular matrix components may include gelatin derived from animals including, but not limited to, pig, cow, horse, chicken, fish, etc. Advantageously, the gelatin can be harvested under sterile conditions from animals in pathogen-free barrier facilities to eliminate the risk of transmission of disease (e.g., hepatitis C, human immunodeficiency virus, etc.)

In situ photopolymerization of GelMA facilitates easy delivery to technically demanding locations such as the cornea, and allows for curing of the bioadhesive exactly according to the required geometry of the tissue to be sealed, which is an advantage over pre-formed materials, as e.g., scaffolds or sheets. Besides physical interconnection of the curing bioadhesive with the tissue surface, gelatin offers additional options to interact with tissues in defect areas. Since gelatin contains multiple domains that bind to cell-surface receptors and extracellular matrix proteins, initial connection of the bioadhesive to corneal tissue as well as subsequent cell attachment to and cell growth on the bioadhesive are promoted.

As used herein, "methacryloyl gelatin" is defined as gelatin having free amines and/or free hydroxyls that have been substituted with at least one methacrylamide group and/or at least one methacrylate group. Gelatin comprises amino acids, some of which have side chains that terminate in amines (e.g., lysine, arginine, asparagine, glutamine) or hydroxyls (e.g., serine, threonine, aspartic acid, glutamic acid). One or more of these terminal amines and/or hydroxyls can be substituted with methacryloyl groups to produce methacryloyl gelatin comprising methacrylamide and/or methacrylate groups, respectively. In some embodiments, with exposure to visible light in the presence of a photoinitiator, the methacryloyl groups on one gelatin molecule can react with the methacryloyl groups on another gelatin molecule to crosslink the methacryloyl gelatin and produce a hydrogel. In some embodiments, the gelatin may be functionalized with methacryloyl groups by reacting gelatin with suitable reagents including, but not limited to, methacrylic anhydride, methacryloyl chloride, etc.

Certain exemplary embodiments of the present invention comprise a photoinitiator. "Photoinitiator" as used herein refers to any chemical compound, or a mixture of compounds, that decomposes into free radicals when exposed to light. Preferably, the photoinitiator produces free radicals when exposed to visible light. Exemplary ranges of visible light useful for exciting a visible light photoinitiator include green, blue, indigo, and violet. Preferably, the visible light has a wavelength in the range of 450-550 nm. Examples of photoinitiators include, but are not limited to, Eosin Y, triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bis(diethylamino)benzophenone, 2-chlorothioxanthen-9-one, 4-(dimethylamino)benzophenone, phenanthrenequinone, ferrocene, diphenyl(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane (Ivocerin®), derivatives thereof, combinations thereof, etc.

In some embodiments, the photoinitiator is a mixture of Eosin Y, triethanolamine, and vinyl caprolactam. In some embodiments, the concentration of Eosin Y is between 0.0125 and 0.5 mM, and/or the concentration of triethanolamine is between 0.1 and 2% (w/v), and/or the concentration of vinyl caprolactam is between 0.05 and 1.5% (w/v). In some embodiments, the concentration of Eosin Y is between 0.025 and 0.15 mM, and/or the concentration of triethanolamine is between 0.2 and 1.6% (w/v), and/or and the concentration of vinyl caprolactam is between 0.09 and 0.8% (w/v). In some embodiments, the concentration of Eosin Y is between 0.025 and 0.15 mM, and/or the concentration of triethanolamine is between 0.2 and 1.6% w/v, and/or the concentration of vinyl caprolactam is between 0.09 and 0.8% (w/v). In some embodiments, the concentration of Eosin Y is between 0.05 and 0.08 mM, and/or the concentration of triethanolamine is between 0.4 and 0.8% (w/v), and/or the concentration of vinyl caprolactam is between 0.18 and 0.4% (w/v). In some embodiments, the concentration of Eosin Y is about 0.05 mM, and/or the concentration of triethanolamine is about 0.4% (w/v), and/or the concentration of vinyl caprolactam is about 0.4% (w/v). In some embodiments, the concentration of Eosin Y is between 0.5 and 0.5 mM, and/or the concentration of triethanolamine is between 0.5 and 2% (w/v), and/or the concentration of vinyl caprolactam is between 0.5 and 1.5% (w/v). In some embodiments, the concentration of Eosin Y is about 0.1 mM, the concentration of triethanolamine is about 0.5% (w/v), and the concentration of vinyl caprolactam is about 0.5% (w/v).

The mechanical properties of Gel-CORE can be tuned for various applications by changing the degree of methacryloyl substitution, GelMA concentration, amount of photoinitiators, and light exposure time. As used herein, the degree of methacryloyl substitution is defined as the percentage of free amines or hydroxyls in the gelatin that have been substituted with methacryloyl groups. In some embodiments, methacryloyl-substituted gelatin has a degree of methacryloyl substitution between 20% and 90%, 30% and 85%, 50% and 90%, 60% and 85%, 65% and 75%, or 70 and 80%. In some embodiments, the methacryloyl-substituted gelatin comprises methacrylamide substitution and methacrylate substitution, and the ratio of methacrylamide substitution to methacrylate substitution is between 80:20 and 99:1, between 90:10 and 98:2, or between 93:7 and 97:3.

As used herein, the concentration of methacryloyl-substituted gelatin is defined as the weight of methacryloyl-substituted gelatin divided by the volume of solvent (w/v), expressed as a percentage. The solvent may be a pharmaceutically acceptable carrier. In some embodiments, the methacryloyl-substituted gelatin is present at a concentration between 5% and 25% (w/v), between 17% and 25% (w/v), between 17% and 23% (w/v), or about 20% (w/v). In some embodiments, the methacryloyl-substituted gelatin is present at a concentration between 5% and 15% (w/v), between 8% and 12% (w/v), or about 10% (w/v). In some embodiments, the methacryloyl-substituted gelatin is present at a concentration between 10% and 40% (w/v), 15% and 35% (w/v), 20% and 30% (w/v), or about 5%, 10%, 15%, 20%, or 25% (w/v).

In some embodiments, the methacryloyl-substituted gelatin has a combination of any of the above degrees of methacryloyl substitution and any of the above concentrations, e.g., a degree of methacryloyl substitution between 50% and 90% and a concentration between 10% and 40% (w/v), a degree of methacryloyl substitution between 60% and 85% and a concentration between 20% and 30% (w/v), a degree of methacryloyl substitution between 70% and 80% and a concentration of 25% (w/v), degree of methacryloyl substitution between 30% and 85% and a concentration between 5% and 15% (w/v), a degree of methacryloyl substitution between 60% and 85% and a concentration between 8% and 12% (w/v), or a degree of methacryloyl substitution between 70% and 80% and a concentration of about 10% (w/v).

Certain exemplary embodiments of the present invention comprise a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation and is compatible with administration to a subject, for example a human. It must also be suitable for use in contact with any tissues or organs with which it may come in contact, meaning that it must not carry a risk of toxicity, irritation, allergic response, immunogenicity, or any other complication that excessively outweighs its therapeutic benefits. Examples of pharmaceutically acceptable carriers include, but are not limited to, a solvent or dispersing medium containing, for example, water, pH buffered solutions (e.g., phosphate buffered saline (PBS), HEPES, TES, MOPS, etc.), isotonic saline, Ringer's solution, polyol (for example, glycerol, propylene glycol, liquid polyethylene glycol, and the like), alginic acid, ethyl alcohol, and suitable mixtures thereof. In some embodiments, the pharmaceutically acceptable carrier can be a pH buffered solution (e.g. PBS) or water.

Corneal cells may be incorporated in or on the surface of the bioadhesive in order to promote corneal tissue formation and healing. Thus, in some embodiments, the GelMA or Gel-CORE composition further comprises corneal cells, preferably epithelial cells, endothelial cells, keratocytes, or a combination thereof. Epithelial and/or endothelial cells are preferably seeded on the surface of the composition, while keratocytes are preferably mixed into the composition prior to photopolymerization.

In order to promote healing and regrowth of the cornea, to prevent or treat infections or immune response, to prevent or treat corneal vessel formation, to treat increased intraocular pressure, or to promote general eye health, the compositions of the present invention may further comprise a therapeutic agent. Non-limiting examples of therapeutic agents include an antibacterial, an anti-fungal, an anti-viral, an anti-acanthamoebal, an anti-inflammatory, an immunosuppressive, an anti-glaucoma, an anti-VEGF, a growth factor, or any combination thereof. Non-limiting examples of antibacterial agents include: penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim sulfamethoxazole, chitosan, ansamycins, daptomycin, nitrofurans, oxazolidinones, bacitracin, colistin, polymixin B, and clindamycin. Non-limiting examples of anti-fungal agents include: amphotericin B, natamycin, candicin, filipin, hamycin, nystatin, rimocidin, voriconazole, imidazoles, triazoles, thiazoles, allylamines, echinocandins, benzoic acid, ciclopirox, flucytosine, griseofulvin, haloprogin, tolnaftate, undecylenic acid, and povidone-iodine. Non-limiting examples of anti-viral agents include: acyclovir, valacyclovir, famciclovir, penciclovir, trifluridine, and vidarabine. Non-limiting examples of anti-acanthamoebal agents include: chlorohexidine, polyhexamethylen biguanide, propamidine, and hexamidine. Non-limiting examples of anti-inflammatory agents include: corticosteroids; non-steroidal anti-inflammatory drugs including salicylates, propionic acid derivatives, acetic acid derivatives, enolic acid derivatives, anthranilic acid derivatives, selective cox-2 inhibitors, and sulfonanilides; biologicals including antibodies (such as tumor necrosis factor-alpha inhibitors) and dominant negative ligands (such as interleukin-1 receptor antagonists). Non-limiting examples of immunosuppressive agents include: alkylating agents, antimetabolites, mycophenolate, cyclosporine, tacrolimus, and rapamycin. Non-limiting examples of anti-glaucoma agents include: prostaglandin analogs, beta blockers, adrenergic agonists, carbonic anhydrase inhibitors, parasympathomimetic (miotic) agents. Non-limiting examples of anti-vascular endothelial growth factor (anti-VEGF) agents include: bevacizumab, ranibizumab, and aflibercept. Non-limiting examples of growth factors include: epidermal growth factor, platelet-derived growth factor, vitamin A, fibronectin, annexin a5, albumin, alpha-2 macroglobulin, fibroblast growth factor b, insulin-like growth factor-I, nerve growth factor, and hepatocyte growth factor.

Certain aspects of the present invention are directed to a composition for corneal reconstruction comprising a crosslinked methacryloyl-substituted gelatin hydrogel and a pharmaceutically acceptable carrier. As used herein, a "hydrogel" is a network of hydrophilic polymer chains forming a colloidal gel. In some embodiments, the crosslinked methacryloyl-substituted gelatin hydrogel has a degree of methacryloyl substitution between 20% and 90%, 40% and 90%, 30 and 85%, 60% and 85%, 65% and 75%, or 70% and 80%. In some embodiments, the crosslinked methacryloyl-substituted gelatin hydrogel is present at a concentration between 5% and 15% (w/v), 8% and 12% (w/v), 10% and 40% (w/v), 15% and 35% (w/v), 20% and 30% (w/v), or about 5%, 10%, 15%, 20%, or 25% (w/v) in the pharmaceutically acceptable carrier. In some embodiments, the crosslinked methacryloyl-substituted gelatin hydrogel has a combination of any of the above degrees of methacryloyl substitution and any of the above concentrations. In some embodiments, the crosslinked methacryloyl-substituted gelatin hydrogel has a degree of methacryloyl substitution between 60% and 80% and a concentration between 10% and 40% (w/v) in the pharmaceutically acceptable carrier, a degree of methacryloyl substitution between 65% and 75% and a concentration between 20% and 30% (w/v), a degree of methacryloyl substitution between 68% and 72% and a concentration of 25% (w/v), a degree of methacryloyl substitution between 30% and 85% and a concentration between 5% and 15% (w/v), a degree of methacryloyl substitution between 60% and 85% and a concentration between 8% and 12% (w/v), or a degree of methacryloyl substitution between 70% and 80% and a concentration of about 10% (w/v).

The physical properties (degradation and mechanical properties, etc.) of Gel-CORE can be modified so that different compositions of the bioadhesive can be made for different purposes, e.g., a bioadhesive with either short or long retention time, appropriate for different clinical scenarios. For example, in the case of a corneal trauma with extruded intraocular contents such as iris, one may wish to apply Gel-CORE for temporary sealing of the injured eye. In patients with corneal epithelial defects, Gel-CORE with short retention time may also be used to cover the epithelial defect. In contrast, in the case of a cornea with a structural defect or severe thinning, Gel-CORE can be formulated in a way that it retains for prolonged periods. Currently available sealant technologies (e.g. cyanoacrylate) do not offer such control in the characteristics of the final product. The following are desired physical properties, either alone or in combination, for bioadhesive compositions suitable for corneal repair. In some embodiments, the composition has a Young's Modulus of 95-100 kPa, 110-140 kPa, or 190-260 kPa. In some embodiments, the composition has an elastic modulus of 5-10 kPa, 10-20 kPa, 25-80 kPa, 5-50 kPa, 5-28 kPa, 10-22 kPa, or 14-18 kPa. In some embodiments, the composition has a compressive modulus of 1-55 kPa, 3-160 kPa, 5-320 kPa, 10-250 kPa, 25-200 kPa, 50-175 kPa or 75-150 kPa. In some embodiments, the composition has a wound closure strength of ≥40 kPa, ≥50 kPa, ≥60 kPa, ≥70 kPa, ≥80 kPa, ≥90 kPa or ≥100 kPa measured using the Wound Closure test (ASTM F2458-05). In some embodiments, the composition has a shear resistance strength of ≥100 kPa, ≥150 kPa, or ≥200 kPa, measured using the Lap Shear test (ASTM F2255-05). In some embodiments, the composition has a burst pressure of ≥15 kPa, ≥17 kPa, or ≥20 kPa, measured using the Burst Pressure test (ASTM F2392-04).

Certain aspects of the present invention are directed to methods for corneal reconstruction, comprising the steps of:

a) applying a composition comprising a methacryloyl-substituted gelatin, a visible light activated photoinitiator, and a pharmaceutically acceptable carrier to a corneal defect; and
b) exposing the composition to visible light.

The mechanical properties of Gel-CORE can be tuned for various applications by changing the visible light exposure time. Without being bound by theory, longer visible light exposure time produces more crosslinkage in the methacryloyl-substituted gelatin, providing a hydrogel with improved mechanical properties, such as adhesion strength, shear strength, compressive strength, tensile strength, etc. In some embodiments, the composition is exposed to visible light for a time period between 30 seconds and 6 minutes, between 1 minute and 5 minutes, between 2 minutes and 4 minutes, or 3 minutes. In some embodiments, the composition is exposed to visible light for a time period of less than one minute, within 10-60 seconds, 15-45 seconds, 20 seconds, or 30 seconds. In some embodiments, the composition is exposed to visible light for a time period between 20 and 120 seconds, or between 30 and 60 seconds. In some embodiments, the composition can be exposed to visible light for a time period between 60 seconds and 240 seconds. In some embodiments, the composition can be exposed to visible light for a time period of about 60 seconds, about 120 seconds, about 180 seconds or about 240 seconds.

In some embodiments, the method does not comprise suturing the cornea. Exemplary ranges of visible light useful for crosslinking the Gel-MA composition include green, blue, indigo, and violet. Preferably, the visible light has a wavelength in the range of 450-550 nm.

Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used to described the present invention, in connection with percentages means±1%, ±1.5%, ±2%, ±2.5%, ±3%, ±3.5%, ±4%, ±4.5%, or ±5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

Exemplary embodiments of the invention can be described by one or more of the following sub paragraphs:

1. A composition for corneal reconstruction comprising a methacryloyl-substituted gelatin (gelatin methacryloyl), a visible light activated photoinitiator, and a pharmaceutically acceptable carrier.
2. The composition of paragraph 1, wherein the methacryloyl-substituted gelatin has a degree of methacryloyl substitution between 30% and 85%.
3. The composition of paragraph 1 or 2, wherein the methacryloyl-substituted gelatin has a degree of methacryloyl substitution between 60% and 85%.
4. The composition of any one of paragraphs 1-3, wherein the methacryloyl-substituted gelatin has a degree of methacryloyl substitution between 70% and 80%.
5. The composition of any one of paragraphs 1-4, wherein the methacryloyl-substituted gelatin comprises methacrylamide substitution and methacrylate substitution, and the ratio of methacrylamide substitution to methacrylate substitution is between 80:20 and 99:1.
6. The composition of paragraph 5, wherein the ratio of methacrylamide substitution to methacrylate substitution is between 90:10 and 98:2.
7. The composition of paragraph 5 or 6, wherein the ratio of methacrylamide substitution to methacrylate substitution is between 92:8 and 97:3.
8. The composition of any one of paragraphs 1-7, wherein the gelatin methacryloyl is present at a concentration between 5% and 25% (w/v).
9. The composition of any of paragraphs 1-8, wherein the gelatin methacryloyl is present at a concentration between 17% and 25% (w/v).
10. The composition of any of paragraphs 1-9, wherein the gelatin methacryloyl is present at a concentration between 17% and 23% (w/v).
11. The composition of any of paragraphs 1-10, wherein the gelatin methacryloyl is present at a concentration of about 20%.
12. The composition of any one of paragraphs 1-8, wherein the gelatin methacryloyl is present at a concentration between 8% and 12% (w/v).
13. The composition of paragraph 12, wherein the gelatin methacryloyl is present at a concentration of about 10% (w/v).
14. The composition of any one of paragraphs 1-13, wherein the visible light activated photoinitiator is selected from the group consisting of: Eosin Y, triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino) benzophenone, 4,4'-bis(diethylamino)benzophenone, 2-chlorothioxanthen-9-one, 4-(dimethylamino)benzophenone, phenanthrenequinone, ferrocene, diphenyl(2, 4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane, derivatives thereof, and any combination thereof.
15. The composition of any of paragraphs 1-14, wherein the visible light activated photoinitiator comprises a mixture of Eosin Y, triethanolamine, and vinyl caprolactam.
16. The composition of paragraph 15, wherein the concentration of Eosin Y is between 0.0125 and 0.5 mM, and/or the concentration of triethanolamine is between 0.1 and 2% (w/v), and/or the concentration of vinyl caprolactam is between 0.05 and 1.5% (w/v).
17. The composition of paragraph 15 or 16, wherein the concentration of Eosin Y is between 0.025 and 0.15 mM, and/or the concentration of triethanolamine is between 0.2 and 1.6% (w/v), and/or and the concentration of vinyl caprolactam is between 0.09 and 0.8% (w/v).
18. The composition of any of paragraphs 15-17, wherein the concentration of Eosin Y is between 0.025 and 0.15 mM, and/or the concentration of triethanolamine is between 0.2 and 1.6% (w/v), and/or the concentration of vinyl caprolactam is between 0.09 and 0.8% (w/v).
19. The composition of any of paragraphs 15-18, wherein the concentration of Eosin Y is between 0.05 and 0.08 mM, and/or the concentration of triethanolamine is between 0.4 and 0.8% (w/v), and/or the concentration of vinyl caprolactam is between 0.18 and 0.4% (w/v).
20. The composition of any of paragraphs 15-19, wherein the concentration of Eosin Y is about 0.05 mM, and/or the concentration of triethanolamine is about 0.4% (w/v), and/or the concentration of vinyl caprolactam is about 0.4% (w/v).
21. The composition of paragraph 15 or 16, wherein the concentration of Eosin Y is between 0.5 and 0.5 mM, and/or the concentration of triethanolamine is between 0.5 and 2% (w/v), and/or the concentration of vinyl caprolactam is between 0.5 and 1.5% (w/v).
22. The composition of any of paragraphs 15, 16 or 21, wherein the concentration of
Eosin Y is about 0.1 mM, the concentration of triethanolamine is about 0.5% (w/v), and the concentration of vinyl caprolactam is about 0.5% (w/v).
23. The composition of any one of paragraphs 1-12, further comprising corneal cells.
24. The composition of paragraph 23, wherein the corneal cells comprise epithelial cells, endothelial cells, keratocytes, or a combination thereof.
25. The composition of any one of paragraphs 1-24, wherein the composition further comprises a therapeutic agent.
26. The composition of paragraph 25, wherein the therapeutic agent is selected from the group consisting of an antibacterial, an anti-fungal, an anti-viral, an anti-acanthamoebal, an anti-inflammatory, an immunosuppressive, an anti-glaucoma, an anti-VEGF, a growth factor, and any combination thereof.
27. A composition for corneal reconstruction comprising a crosslinked gelatin methacryloyl hydrogel and a pharmaceutically acceptable carrier, wherein the crosslinked methacryloyl-substituted gelatin (gelatin methacryloyl) hydrogel has a degree of methacryloyl substitution between 30% and 85% and a concentration between 5% and 25% (w/v) in the pharmaceutically acceptable carrier.
28. The composition of paragraph 27, wherein the concentration is between 5% and 15% (w/v).
29. The composition of paragraph 27 or 28, wherein the crosslinked gelatin methacryloyl hydrogel has a degree of methacryloyl substitution between 60% and 85% and a concentration between 8% and 12% (w/v).
30. The composition of any of paragraphs 27-29, wherein the crosslinked gelatin methacryloyl hydrogel has a degree of methacryloyl substitution between 70% and 8% and a concentration of about 10% (w/v).
31. The composition of paragraph 27, wherein the concentration is between 17% and 25% (w/v).
32. The composition of paragraph 27 or 28, wherein the crosslinked gelatin methacryloyl hydrogel has a degree of methacryloyl substitution between 60% and 85% and/or a concentration between 17% and 23% (w/v).
33. The composition of any of paragraphs 27-29, wherein the crosslinked gelatin methacryloyl hydrogel has a degree of methacryloyl substitution between 70% and 80% and/or a concentration of about 20% (w/v).
34. The composition of any one of paragraphs 27-33, having a Young's Modulus of 190-260 kPa or 250-350 kPa.
35. The composition of any one of paragraphs 27-33, having a Young's Modulus of 110-140 kPa or 100-150 kPa.
36. The composition of any one of paragraphs 27-35, having an elastic modulus of 5-50 kPa.
37. The composition of any one of paragraphs 27-36, having a compressive modulus of 5-320 kPa or 10-250 kPa.
38. The composition of any one of paragraphs 27-37, having a compressive modulus of 5-160 kPa or 125-175 kPa.
39. The composition of any one of paragraphs 27-38, having a wound closure strength of ≥40 kPa.
40. The composition of any one of paragraphs 27-38, having a wound closure strength of ≥45 kPa.
41. The composition of any one of paragraphs 27-40, having a burst pressure of ≥10 kPa or ≥15 kPa.
42. The composition of any one of paragraphs 27-41, wherein the composition further comprises a therapeutic agent.
43. The composition of paragraph 42, wherein the therapeutic agent is selected from the group consisting of an antibacterial, an anti-fungal, an anti-viral, an anti-acanthamoebal, an anti-inflammatory, an immunosuppressive, an anti-glaucoma, an anti-VEGF, a growth factor, and any combination thereof.
44. The composition of any one of paragraphs 27-43, further comprising corneal cells.
45. The composition of paragraph 44, wherein the corneal cells comprise epithelial cells, endothelial cells, keratocytes, or a combination thereof.
46. The composition of any one of paragraphs 27-45, which is substantially transparent.
47. The composition of any one of paragraphs 27-46, comprising a substantially smooth surface.

48. A method for corneal reconstruction, comprising the steps of:
   a. applying a composition comprising a methacryloyl-substituted gelatin, a visible light activated photoinitiator, and a pharmaceutically acceptable carrier to a corneal defect; and
   b. exposing the composition to visible light.
49. The method of paragraph 48, wherein the methacryloyl-substituted gelatin has a degree of methacryloyl substitution between 30% and 85%.
50. The method of paragraph 48 or 49, wherein the methacryloyl-substituted gelatin has a degree of methacryloyl substitution between 60% and 85%.
51. The method of any one of paragraphs 48-50, wherein the methacryloyl-substituted gelatin has a degree of methacryloyl substitution between 70% and 80%.
52. The method of any one of paragraphs 48-51, wherein the methacryloyl-substituted gelatin comprises methacrylamide substitution and methacrylate substitution, and the ratio of methacrylamide substitution to methacrylate substitution is between 80:20 and 99:1.
53. The method of paragraph 52, wherein the ratio of methacrylamide substitution to methacrylate substitution is between 90:10 and 98:2.
54. The method of paragraph 52 or 53, wherein the ratio of methacrylamide substitution to methacrylate substitution is between 92:8 and 97:3.
55. The method of any one of paragraphs 48-54, wherein the methacryloyl-substituted gelatin is present at a concentration between 5% and 25% (w/v).
56. The method of any one of paragraphs 48-55, wherein the methacryloyl-substituted gelatin is present at a concentration between 17% and 25% (w/v).
57. The method of any one of paragraphs 48-56, wherein the methacryloyl-substituted gelatin is present at a concentration between 17% and 23% (w/v).
58. The method of any one of paragraphs 48-57, wherein the methacryloyl-substituted gelatin is present at a concentration of about 20%.
59. The method of any one of paragraphs 48-55, wherein the methacryloyl-substituted gelatin is present at a concentration between 8% and 12% (w/v).
60. The method of paragraph 59, wherein the methacryloyl-substituted gelatin is present at a concentration of about 10% (w/v).
61. The method of any one of paragraphs 48-60, wherein the visible light activated photoinitiator is selected from the group consisting of: Eosin Y, triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bis(diethylamino)benzophenone, 2-chlorothioxanthen-9-one, 4-(dimethylamino)benzophenone, phenanthrenequinone, ferrocene, diphenyl(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane, derivatives thereof, and any combination thereof.
62. The method of any one of paragraphs 48-61, wherein the visible light activated photoinitiator comprises a mixture of Eosin Y, triethanolamine, and vinyl caprolactam.
63. The method of paragraph 62, wherein the concentration of Eosin Y is between 0.0125 and 0.5 mM, and/or the concentration of triethanolamine is between 0.1 and 2% w/v, and/or the concentration of vinyl caprolactam is between 0.05 and 1.5% w/v.
64. The method of paragraph 62 or 63, wherein the concentration of Eosin Y is between 0.025 and 0.15 mM, and/or the concentration of triethanolamine is between 0.2 and 1.6% w/v, and/or and the concentration of vinyl caprolactam is between 0.09 and 0.8% w/v.
65. The method of any of paragraphs 62-64, wherein the concentration of Eosin Y is between 0.025 and 0.15 mM, and/or the concentration of triethanolamine is between 0.2 and 1.6% w/v, and/or the concentration of vinyl caprolactam is between 0.09 and 0.8% w/v.
66. The method of any of paragraphs 62-65, wherein the concentration of Eosin Y is between 0.05 and 0.08 mM, and/or the concentration of triethanolamine is between 0.4 and 0.8% w/v, and/or the concentration of vinyl caprolactam is between 0.18 and 0.4% w/v.
67. The method of any of paragraphs 62-66, wherein the concentration of Eosin Y is about 0.05 mM, and/or the concentration of triethanolamine is about 0.4% w/v, and/or the concentration of vinyl caprolactam is about 0.4% w/v.
68. The method of paragraph 62 or 63, wherein the concentration of Eosin Y is between 0.5 and 0.5 mM, and/or the concentration of triethanolamine is between 0.5 and 2% w/v, and/or the concentration of vinyl caprolactam is between 0.5 and 1.5% w/v.
69. The composition of any of paragraphs 62, 63 or 68, wherein the concentration of Eosin Y is about 0.1 mM, the concentration of triethanolamine is about 0.5% w/v, and the concentration of vinyl caprolactam is about 0.5% w/v.
70. The method of any one of paragraphs 48-69, wherein the composition is exposed to visible light with a wavelength in the range of 450 to 550 nm.
71. The method of any one of paragraphs 48-70, wherein the composition is exposed to visible light for a time period between 20 and 120 seconds.
72. The method of any one of paragraphs 48-71, wherein the composition is exposed to visible light for a time period between 30 and 60 seconds.
73. The method of any one of paragraphs 48-72, wherein the composition further comprises a therapeutic agent.
74. The method of paragraph 73, wherein the therapeutic agent is selected from the group consisting of an antibacterial, an anti-fungal, an anti-viral, an anti-acanthamoebal, an anti-inflammatory, an immunosuppressive, an anti-glaucoma, an anti-VEGF, a growth factor, and any combination thereof.
75. The method of any one of paragraphs 48-74, wherein the composition further comprises corneal cells.
76. The method of paragraph 75, wherein the corneal cells comprise epithelial cells, endothelial cells, keratocytes, or a combination thereof.
77. The method of any one of paragraphs 48-76, wherein the composition is substantially transparent.
78. The method of any one of paragraphs 48-77, wherein the method does not comprise suturing the cornea.

It is noted that the invention provides an improved bioadhesive for repair and reconstruction of defects and injuries to the cornea. Following ASTM standard tests, crosslinked methacryloyl-substituted gelatin hydrogels of the present invention (Gel-CORE) were shown to exhibit adhesive properties, i.e. wound closure strength, shear resistance and burst pressure, that were suitable for application to the cornea. In vitro experiments showed that Gel-CORE is cytocompatible with corneal cells and promotes cell integration after application. In vivo experiments in rabbits showed that Gel-CORE can effectively seal corneal defects. Advantageously, the bioadhesives of the present invention are low cost, easy to produce, and easy to use, making them a promising substance to be used for corneal repair, as well as an easily tunable platform to further optimize the adhesive characteristics.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

EXAMPLES

The disclosure is further illustrated by the following examples which should not be construed as limiting. The examples are illustrative only, and are not intended to limit, in any manner, any of the aspects described herein. The following examples do not in any way limit the invention.

Example 1: Advantages and Applications of Gel-CORE

Gel-CORE bioadhesive may advantageously be used for the following applications:

Filling Corneal Defects:

Gel-CORE can fill corneal defects and corneal thinning disorders, which occur not only from physical injuries but also after a wide array of corneal inflammatory disorders, such as microbial keratitis and immune-mediated corneal melts. In such cases, the bioadhesive is used to provide structural support in the emergency setting. In addition, in long-term it allows regeneration of corneal cells into the bioadhesive, which acts as a stromal replacement technology without the need to use the traditional treatment modalities such as corneal transplantation and tissue patch graft.

The current standards of care for repair of corneal stromal defects and thinning include tissue/patch grafting or glue application. Corneal transplantation and patch grafting require donor tissues, which may not be available. In addition, the use of allogeneic tissues for grafting carries a risk for immune reactions.

Currently, there is no approved adhesive for filling corneal defects. Although cyanoacrylate glue is currently used as "off-label" for treating many emergent ophthalmic settings such as corneal perforations, impending perforations and progressive corneal thinning disorders, it has several major drawbacks, including:

i. Low biocompatibility, with cytotoxic effects on the cornea and other ocular tissues (risk of cataract formation and retinopathy if it enters the eye);
  ii. Lack of transparency, precluding good vision and impairing view of retrocorneal structures;
  iii. Risk of secondary infection due to high porosity;
  iv. Difficult to control its application, with glue potentially falling off unpredictably;
  v. Rough surface requiring contact lens wear, which adds additional infection risk; and
  vi. Does not integrate with corneal tissue.

In contrast, Gel-CORE has several advantages as compared to currently available adhesives for corneal repair and sealing.

1. Biosafety:

Gel-CORE has superior biocompatibility since its base material is gelatin, which is a naturally derived biopolymer from collagen that has been used in different medical applications, raising little safety concerns over other materials (e.g. cyanoacrylate-based products). In addition, by selecting a visible light activated photoinitiator, the potential damage associated with UV exposure in previous formulations will be avoided.

2. Tunable Properties:

the physical properties (degradation and mechanical properties, etc.) of Gel-CORE can be modified so that different compositions of the bioadhesive can be made for different purposes—a bioadhesive with either short or long retention time, appropriate for different clinical scenarios. For example, in the case of a corneal trauma with extruded intraocular contents such as iris, one may wish to apply Gel-CORE for temporary sealing of the injured eye. In contrast, in the case of a cornea with a structural defect or severe thinning, Gel-CORE can be formulated in a way that it retains for prolonged periods. Currently available sealant technologies (e.g. cyanoacrylate) do not offer such control in the characteristics of the final product.

3. Transparency:

in ex vivo experiments with the rabbit cornea, Gel-CORE has been demonstrated to be transparent with a smooth and convex surface that can retain the normal corneal contour after administration and photopolymerization on a 50%-deep corneal injury (FIG. 1A-1E).

4. Reversibility:

unlike cyanoacrylate where the application leads to immediate hardening, Gel-CORE requires application of light for hardening; thus a misapplication can be reversed if needed.

5. High Adhesion and Retention:

Gel-CORE has high adhesion to tissues based on wound closure, lap shear, burst pressure, and ex vivo adhesion tests. In addition, ex vivo data has consistently shown that Gel-CORE is retained for many days with the bioadhesive remaining uncompromised and completely attached to the cornea.

6. Corneal Tissue Regeneration:

unlike the other adhesives used for cornea sealing (e.g. cyanoacrylate), Gel-CORE permits both tissue sealing and regeneration. Human corneal keratocytes can grow within Gel-CORE. Gel-CORE will adhere to the cornea strongly, and be retained while the tissue is undergoing physiological repair/regeneration.

Sealing Corneal, Limbal, or Scleral Wounds:

The traditional treatment for such wounds includes suturing. However, suturing is associated with substantial drawbacks which include the following: 1. Sutures are foreign bodies that can serve as risk factors for microbial entrapment and infection, inflammation, and neovascularization. 2. Corneal sutures often induce regular or irregular astigmatism, leading to impaired visual acuity. To avoid these drawbacks, sealants have been used to seal wounds. The only approved sealants ReSure® (in the U.S.) and OcuSeal® (in the Europe) are for sealing corneal incisions of cataract surgery. However, they fall off quickly. In contrast, Gel-CORE which strongly seals the corneal, limbal, or scleral wounds can be tuned to provide the sealing for a desired longer time. Gel-CORE can provide adhesion for closure of corneal wounds. In such conditions, it allows sealing the wound without the need for suturing. Gel-CORE can provide adhesion for closure of limbal and scleral wounds. In such conditions, it allows sealing the wound without the need for suturing.

Covering Corneal Epithelial Defects:

The traditional treatment for patients with corneal epithelial defect includes eye patching, bandage contact lens, and sometime an invasive procedure. However, these options are limited by the fact that they can be bothersome for the patient and can increase the risk of corneal infections. For these cases, in contrast, we can use a fast-degrading formulation of Gel-CORE to protect the cornea while corneal epithelium regenerates itself.

Temporary Protection of Intraocular Structures in Cases with Corneal or Scleral Lacerations and Prolapse of Intraocular Structures:

The only available treatment option for such cases is surgical repositioning of intraocular structures with suturing the wounds which should be performed by a skilled surgeon in an equipped facility. However, this will delay the surgical procedure which predisposes the patient to intraocular infection. In contrast, the use of Gel-CORE provides a temporary support for cornea/sclera and intraocular structures while preventing infection. A permanent repair can later be performed without imposing a high risk of intraocular infection. Gel-CORE can be used in cases with extensive corneal/scleral injuries associated with iris/choroid-retina prolapse as a therapeutic agent (e.g. antibiotic, etc.)-containing biologic patch to cover intraocular structures. In such cases, it protects the intraocular structures and prevents infection before a permanent surgical procedure is performed.

Corneal Infections with or without Significant Thinning:

The current standard of care for corneal infection includes frequent instillation of eye drops, which is cumbersome for the patient. To avoid this drawback, currently there are some studies using contact lenses with slow-release antibiotic. However, such technologies do not provide any structural support for the cornea. In contrast, Gel-CORE not only can provide extended release of antibiotic(s) but also provide the structural support for the cornea with infectious keratitis. Gel-CORE can be used in cases of corneal infections with and without significant thinning as an antibiotic-containing patch which provides an extended release of antibiotic(s) in addition to a structural support for the cornea.

Inflammatory Corneal Thinning:

The current standard of care for inflammatory corneal thinning includes use of topical or systemic anti-inflammatory medications. For significant thinning, a surgical procedure is performed as described above for corneal stromal defects. In contrast, Gel-CORE not only provides structural support as described above for corneal defects, but also can act as a drug reservoir to slowly release anti-inflammatory medications, thereby obviating or reducing the need for additional topical or systemic medications. Thus, Gel-CORE can be used as a platform for drug delivery as the bioadhesive is clear and can be retained for many weeks based on the therapeutic use. Gel-CORE can be used in cases of inflammatory corneal thinning as an anti-inflammatory-containing patch, which provides an extended release of anti-inflammatory medication(s) in addition to providing structural support for the cornea.

Refractive Corneal Modeling:

Although various intracorneal implants have previously been used for refractive modeling of the cornea, including PermaVision (ReVision Optics), Kamra (AcoFocus), Flexivue Microlens (Presbia), and Raindrop inlay (Revision Optics), they are all associated with deposit or haze formation due to lack of complete biocompatibility with the corneal tissue. In contrast, Ge-CORE has high degree of biocompatibility which prevents it from these complications. In addition, in Gel-CORE there is integration of the corneal cells with the biomaterial which will not happen in other inlays. Gel-CORE can be used as an intracorneal implant for corneal modeling to change the refractive power of the cornea in patients with refractive error (myopia, hyperopia, astigmatism, and presbyopia).

Replacement of Corneal Tissue in Transplantation:

Although various artificial corneas have previously been used to replace the corneal tissue in transplantation, including Boston Keratoprosthesis, osteoodontokeratoprosthesis, AlphaCor, they suffer from the fact that there is no integration of corneal cells into these artificial corneas. In contrast, Gel-CORE shows a high degree of migration and integration of native corneal cells into the biomaterial. Gel-CORE can be used as a replacement of corneal tissue in lamellar corneal transplantation instead of using donor corneal tissue. Gel-CORE can also be used as a replacement of corneal tissue in full-thickness corneal transplantation (similar to artificial cornea).

Example 2: Synthesis of Gelatin Methacryloyl (GelMA) Prepolymer

GelMA was synthesized as previously described.[14] Concentrations of gelatin and methacrylic anhydride may be varied to produce GelMA having the ranges of methacryloyl substitution disclosed herein. For example, 10% (w/v) porcine gelatin (Sigma-Aldrich, St. Louis, Mo., USA) was dissolved in phosphate-buffered saline (PBS) and heated at 60° C. for 20 minutes. Dropwise addition of 8% (v/v) methacrylic anhydride (Sigma-Aldrich, St. Louis, Mo., USA) under continuous stirring at 50° C. for 3 hours was followed by dilution with PBS and dialysis against deionized water at 40-50° C. for 7 days. After sterile filtration and lyophilization for 4 days, GelMA was stored at −80° C. until experimental use.

Quantification of Methacrylamide Groups.

Figure 2A:
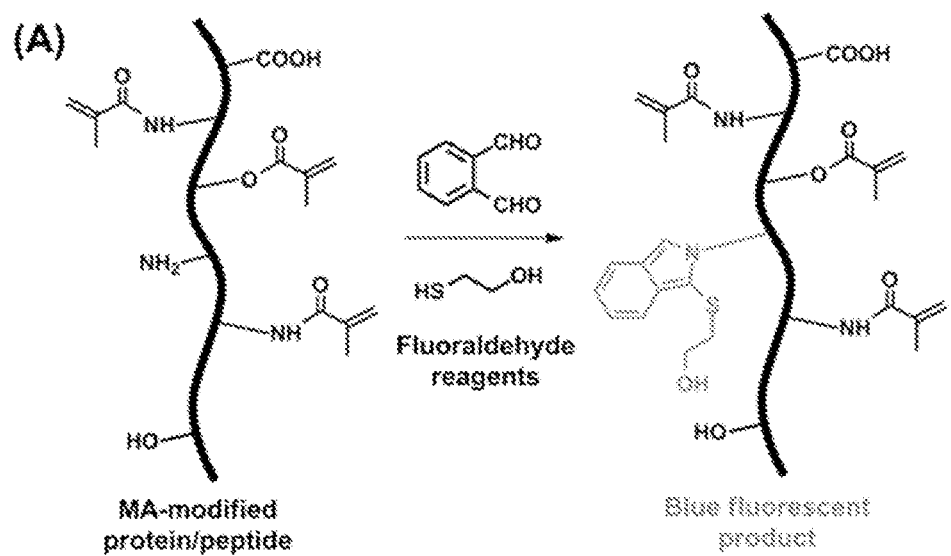
FIG. 2A is a reaction scheme showing fluoraldehyde assay to determine conversion of amine groups in GelMA. The reaction between unmodified lysine residues in methacrylic anhydrate (MA)-modified materials and the fluoraldehyde reagents generates blue fluorescent derivatives, which show excitation and emission maxima at wavelengths of 340 nm and 455 nm, respectively.
Figure 2B:
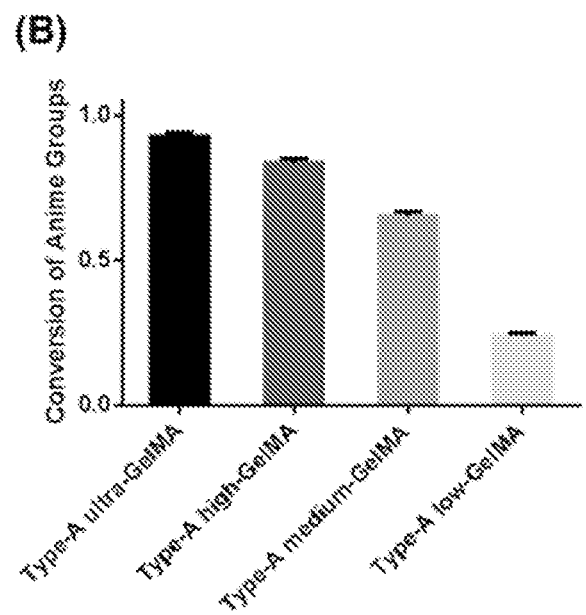
FIG. 2B is a bar graph showing conversions of amine groups in GelMA samples. Gelatin is used as the control.

Conversion of amine groups in biomaterials such as GelMA has been conventionally determined using a proton nuclear magnetic resonance ($^1$H NMR) spectrum.[13-14] However, since gelatin is a mixture of polypeptides with complicated compositions, it might not be feasible to detect and differentiate the resonance peaks from methacrylamide and methacrylate groups from $^1$H NMR spectra. Instead, a fluoraldehyde assay[43] allows for easier and more accurate determination of the conversion of amine groups. When the modified protein/peptide samples are mixed with the assay solution containing o-phthalaldehyde and 2-mercaptoethanol, all the remaining primary amine groups in the materials will be converted into fluorescent species with blue emissions (FIG. 2A). Four distinct GelMA formulations were prepared that vary in their degree of methacryloyl substitution by adding different amounts of MA to the reaction (Table 1).[14] Depending on the degree of modification, the resulting GelMA formulations will be referred to as ultra-GelMA, high-GelMA, medium-GelMA, and low-GelMA, respectively. Using gelatin as the standard, the amount of remaining primary amine groups can be easily obtained. The conversions of amine groups of the resulting GelMA samples were determined using the fluoraldehyde assay as ~93% for ultra-GelMA, ~84% for high-GelMA, ~65% for medium-GelMA, and ~24% for low-GelMA, respectively (FIG. 2B). It is clear that the conversion of amine groups is positively correlated with the added MA amount at a fixed reaction temperature and reaction time.

TABLE 1

Summary of molecular parameters of different GelMA samples.

| Samples | Conversion of amine groups | Estimated amount of methacrylamide groups (mmol/g) | Estimated amount of methacrylate groups (mmol/g) | Preparation conditions |
|---|---|---|---|---|
| Type-A Ultra-GelMA | 93% | 0.46$^a$ | 0.034 | 20% (v/v) MA, 50° C., 3 h |
| Type-A High-GelMA | 84% | 0.42$^a$ | 0.028 | 8% (v/v) MA, 50° C., 3 h |
| Type-A Medium-GelMA | 65% | 0.32$^a$ | 0.022 | 5% (v/v) MA, 50° C., 3 h |
| Type-A Low-GelMA | 24% | 0.12$^a$ | 0.008 | 0.5% (v/v) MA, 50° C., 3 h |

Quantification of Methacrylate Groups.

In our previous publications on preparation of GelMA,[14] $^1$HNMR spectra were used to determine the conversion of amine groups by calculations based on the integration areas of the resonance peak from the amine groups. Quantification of the methacrylate groups was unable to perform due to the lack of distinguishable resonance peaks of the hydroxyl groups in $^1$HNMR spectra of the modified peptide or protein samples.

Figures 3A, 3B, 3C, 3D, 3E:
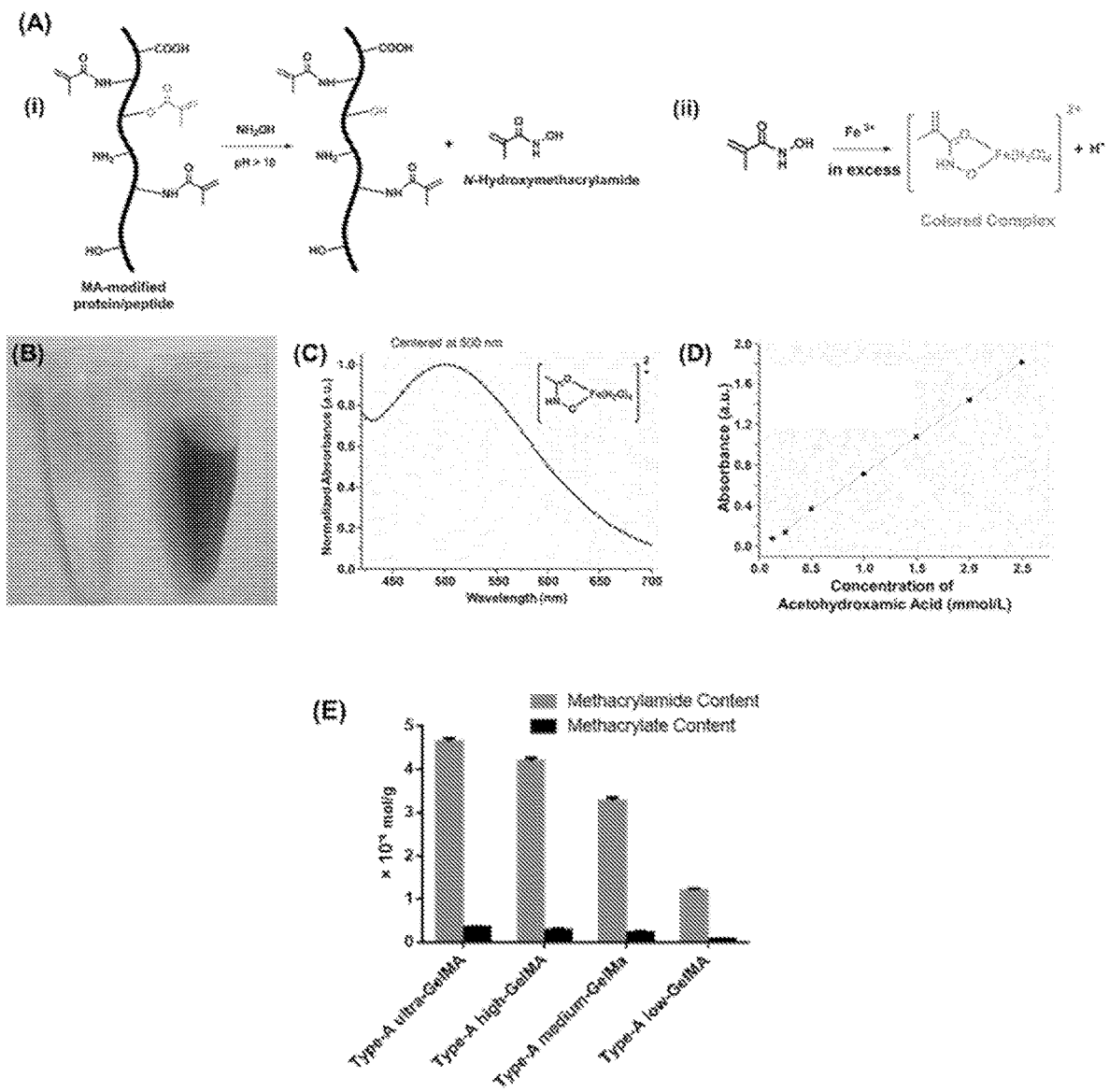
FIGS. 3A-3E show Fe(III)-hydroxamic acid assay for quantification of methacrylate groups in GelMA.

Here, a Fe(III)-hydroxamic acid-based assay was used to determine the amount of methacrylate groups in different GelMA samples (FIG. 3A-3E). Hydroxamic acid forms a brown-red complex with Fe(III) ions, which can serve as a qualitative test for hydroxamic acid species (FIG. 3A). This class of complexes has an absorption peak centered at around 500 nm (FIGS. 3B and 3C). Formation of the Fe(III)-hydroxamic acid complexes has been used to quantify the reactivity of amine groups and hydroxyl groups of lysozymes with several different carboxylic acid anhydrides,[44] along with other analytic applications such as the quantification of ester group residues in poly(vinyl alcohol).[45] Acetohydroxamic acid (AHA) was used as the standard to establish the working curve and it is assumed that the complex of acetohydroxamic acid and Fe(III) ions (FeAHA) have similar spectrophotometric properties with that of N-hydroxymethacrylamide and Fe(III) ions (FeHMA).[44] Iron(III) perchlorate was dissolved in dilute hydrochloric acid to prepare the Fe(III) ion solutions, which were added to the acetohydroxamic acid solutions in large excess to form a 1:1 complex. It has been reported that the apparent extinction coefficient reaches its maximum when the molar ratio of Fe(III) and hydroxamic acid was over 20 and will remain independent on the ratio[46]. UV-Vis absorption spectra of the series of standard FeAHA solutions were recorded in UV-transparent microplate covering the concentrations of from $1.3 \times 10^{-4}$ to $2.5 \times 10^{-3}$ mol/L. Indeed, excellent linearity was achieved when the absorbance was plotted as a function of AHA concentration and analyzed with a linear least-square fit (FIG. 3D).

To determine the amount of methacrylate groups in GelMA samples, an aminolysis reaction to convert the methacrylate groups to the detectable N-hydroxymethacrylamide compound was employed. In particular, GelMA samples at 50 mg/mL were treated with hydroxylamine solutions at room temperature for 10 min to generate N-hydroxymethacrylamide. The resulting solution was acidified with hydrochloric acid, followed by the addition of excess Fe(III) ions. Color change upon the addition of Fe(III) ions indicated the formation of the FeHMA complex, which confirmed the existence of methacrylate groups. Concentrations of the FeHMA complex formed in situ were determined from the UV-Vis absorption spectra, which could be used to calculate the amounts of methacrylate groups in the GelMA samples (FIG. 3E). For all tested GelMA samples, it was found that methacrylate groups represented below 10% of all methacryloyl substitutions. These results suggested that the amine groups are indeed more reactive than the hydroxyl groups, and the methacrylamide groups are the dominant form in GelMA (FIG. 3E).

Example 3: Preparation and Material Characterization of Gel-CORE Hydrogels

Figures 4A, 4B, 4C:
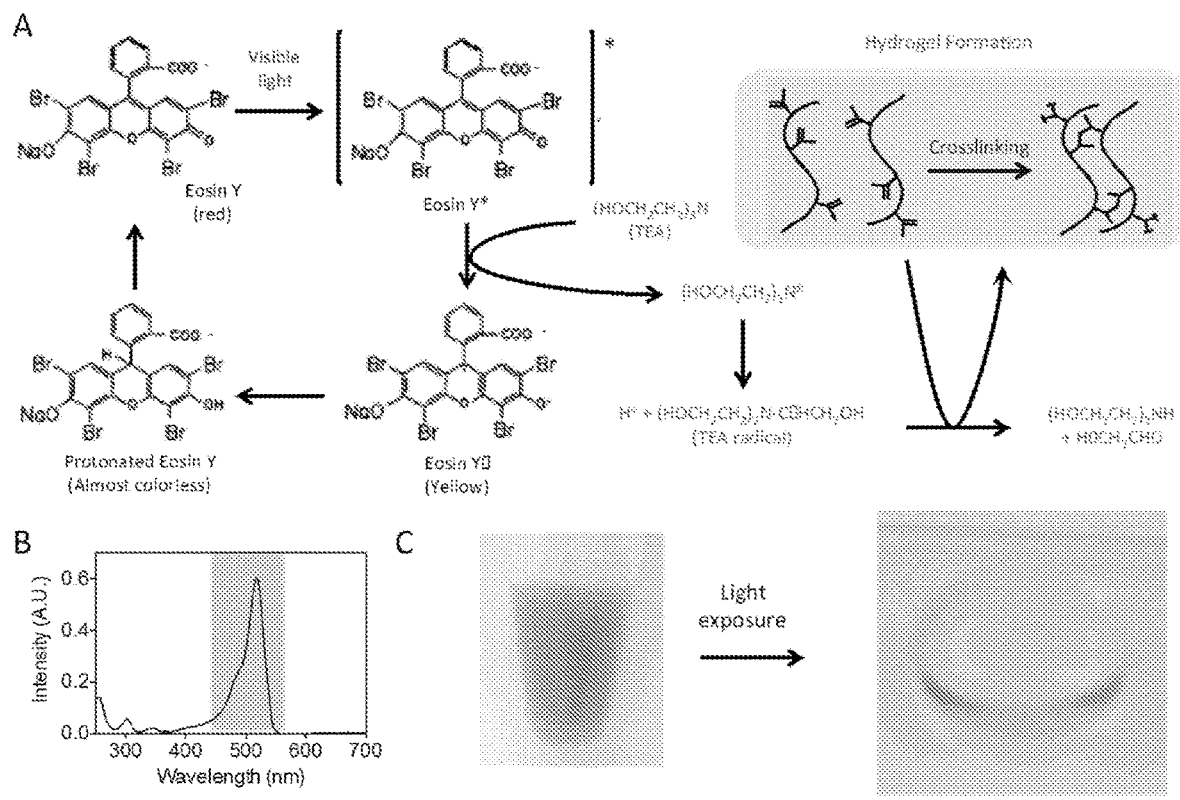
FIGS. 4A-4C show an exemplary Eosin-Y-based photopolymerization system of the invention.
Figures 5A, 5B:
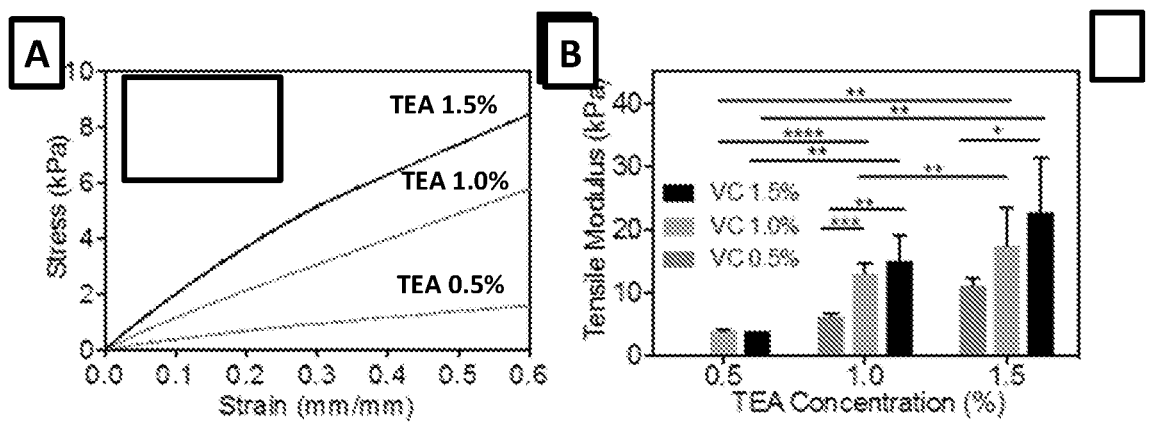
FIGS. 5A-5B show visible light crosslinked GelMA hydrogel with tunable (FIGS. 5A and 5B) mechanical properties—Stress vs strain (FIG. 5A) and Tensile Modulus vs TEA concentration (FIG. 5B). ($*p<0.05$, $p<0.01$, $*p<0.001$ and $****p<0.0001$)
Figures 6A, 6B:
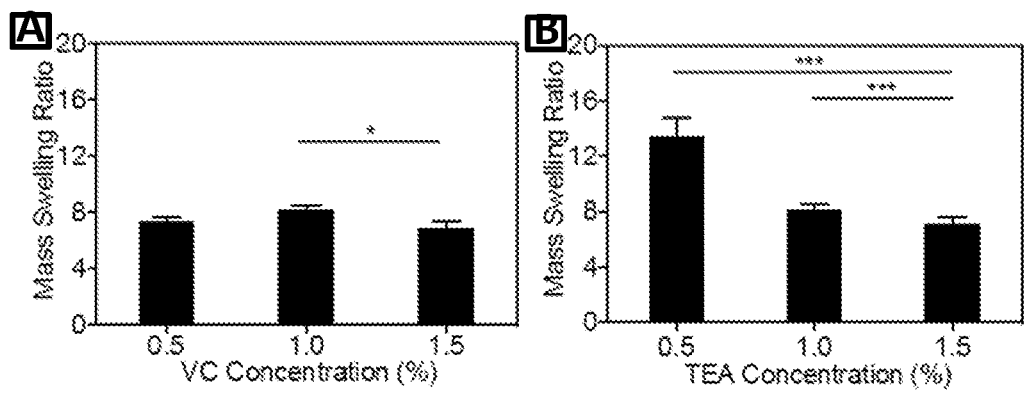
FIGS. 6A-6B show visible light crosslinked GelMA hydrogel with tunable swelling ratio varying VC concentrations (FIG. 6A) and TEA concentrations (FIG. 6B).

Visible light crosslinkable Gel-CORE was made by using Eosin-Y (Sigma-Aldrich) as a visible-light activated initiator, triethanolamine (TEOA) (Sigma-Aldrich) as a co-initiator, and vinyl caprolactam (VC) (Sigma-Aldrich) as a catalyst.[15,16] Using this crosslinking system, polymerization of methacryloyl groups on GelMA was initiated through exposure to blue light (450-550 nm, Xenon source) at 100 mW/cm$^2$ (FIGS. 4A-4C). Eosin-Y is a water-soluble xanthene dye and is a common stain for collagen, the main component of the cornea and sclera. This visible light system has a well-established track record of biocompatibility in a range of applications[15-19] and has gained FDA approval for use in the human body in the polyethylene glycol (PEG)-based sealant FocalSeal® (Genzyme Biosurgical, Cambridge, Mass.). Visible light crosslinkable Gel-CORE hydrogels show tunable physical properties (FIGS. 5A-5B); the elastic modulus of Gel-CORE hydrogels using visible light crosslinking could be tuned from 5-28 kPa (FIGS. 5A-5B). In addition, the swelling ratio could be changed from 7% to 13% (w/w) (FIG. 6B).

To form the hydrogels, GelMA with different degrees of methacryloyl modification (30%-85%) can be used.[14] Then, different concentrations of GelMA prepolymer solutions (5-15% w/v) can be prepared in phosphate buffered saline (PBS) containing Eosin-Y (0.1-0.5 mM), TEOA (0.5-2% w/v), and VC (0.5-1.5% w/v). The formulated GelMA prepolymer solutions can be photocrosslinked by exposure to blue light for 20-120 seconds, which matches the absorption spectrum of Eosin-Y (FIG. 4B). Varying the GelMA concentration, Eosin-Y/TEOA/VC concentrations, and light exposure time varies the physical properties of the engineered hydrogels.

As the formulations are used to repair the cornea, the Gel-CORE hydrogels should have similar elasticity and stiffness to the native cornea (Young Modulus: 250-350 kPa). The swelling ratio of the hydrogel should be optimized to obtain swelling ratio of <20% to ensure that the adhesive preserves its shape after being applying in the corneal defect. In particular, the swelling ratio can affect the shape, curvature and the smoothness of the sealed defect.

For example, freeze-dried GelMA produced according to Example 2 was dissolved in PBS at a concentration of 10% (w/v). After addition of a photoinitiator mixture of 0.1% (w/v) Eosin Y, 0.5% (w/v) triethanolamine, and 0.5% (w/v) vinyl caprolacatam and dissolving at 80° C., the prepolymer solution was photocrosslinked to a hydrogel (Gel-CORE) by visible light irradiation (450-550 nm, Xenon source, 100 mW/cm$^2$).

In another example, different concentrations of GelMA (5, 10, 15, 20% (w/v)) were tested for material characterization. Freeze-dried GelMA (as produced in Example 2) was dissolved in PBS containing 1.875% (w/v) triethanolamine (TEA) and 1.25% (w/v) N-vinylcaprolactam (VC) at concentrations of 5, 10, 15, 20% (w/v). Eosin Y was separately dissolved in fresh DPBS at a concentration of 0.5 mM. To prepare the hydrogel, 8 µL, of GelMA solution was mixed with 2 µL of Eosin Y solution, and then the mixture was placed between two glass coverslips separated by 150 µm spacers, followed by exposure to blue-green light (100 mW/cm$^2$, Xenon source from Genzyme Biosurgery) in the range of 450 to 550 nm for 20 sec.

Mechanical testing of Gel-CORE samples was conducted as previously published.[14] Briefly, prepolymer solution was photocrosslinked to produce the following geometries: discs for compressive testing (n=3 to 5; 6 mm in diameter and 1.5 mm in height) and cuboids for tensile testing (n=7 to 10; 3 mm in width, 14 mm in length and 1.5 mm in thickness). The hydrogels were either directly analyzed or stored in PBS at 4° C. for 24 hours before being examined on an mechanical testing system 5542 (Instron, Norwood, Mass., USA). The strain rate was set to 1 mm/min for compressive testing and tensile testing. The compressive strength and the ultimate tensile strength of the samples were determined at the point of breaking or tearing of the hydrogels. The compressive modulus and elastic modulus were obtained by measuring the slope of stress/strain curves at strain rate between 0-0.5%.

In order to analyze the swelling characteristics, Gel-CORE hydrogel samples (n=5) were allowed to swell in PBS for 1, 2 or 3 days. At the end of the experiment, excess liquid was gently removed with a tissue, and the wet weight was measured. After lyophilization, the dry weight of the samples was measured, and the swelling ratio was calculated as (wet weight-dry weight)/dry weight (FIGS. 6A and 6B).

Ex vivo test for Gel-CORE hydrogels used explanted rabbit cornea tissues. GelMA prepolymer was first applied on incision created on the explanted cornea and then photocrosslinked by exposure to visible light using optimized light exposure time. The burst pressure was then measured by using a pressure sensor after air inflation into the cornea. For example, a rabbit cornea was sealed with Gel-CORE (10% (w/v), prepolymer concentration, 5 mM Eosin-Y, and exposure time of 120 sec. The incision created on rabbit cornea was tightly and completely sealed with Gel-CORE and the tissue could be pressurized up to around 3.5 kPa (26 mmHg), which is double of the pressure of healthy eye.

Preferably, Gel-CORE samples have a burst pressure higher than 15 kPa (>110 mm Hg),[20-21] a lap shear strength >100 kPa, adhesion strength >40 kPa, and photopolymerize in <60 seconds of light exposure.

Figures 7A, 7B, 7C:
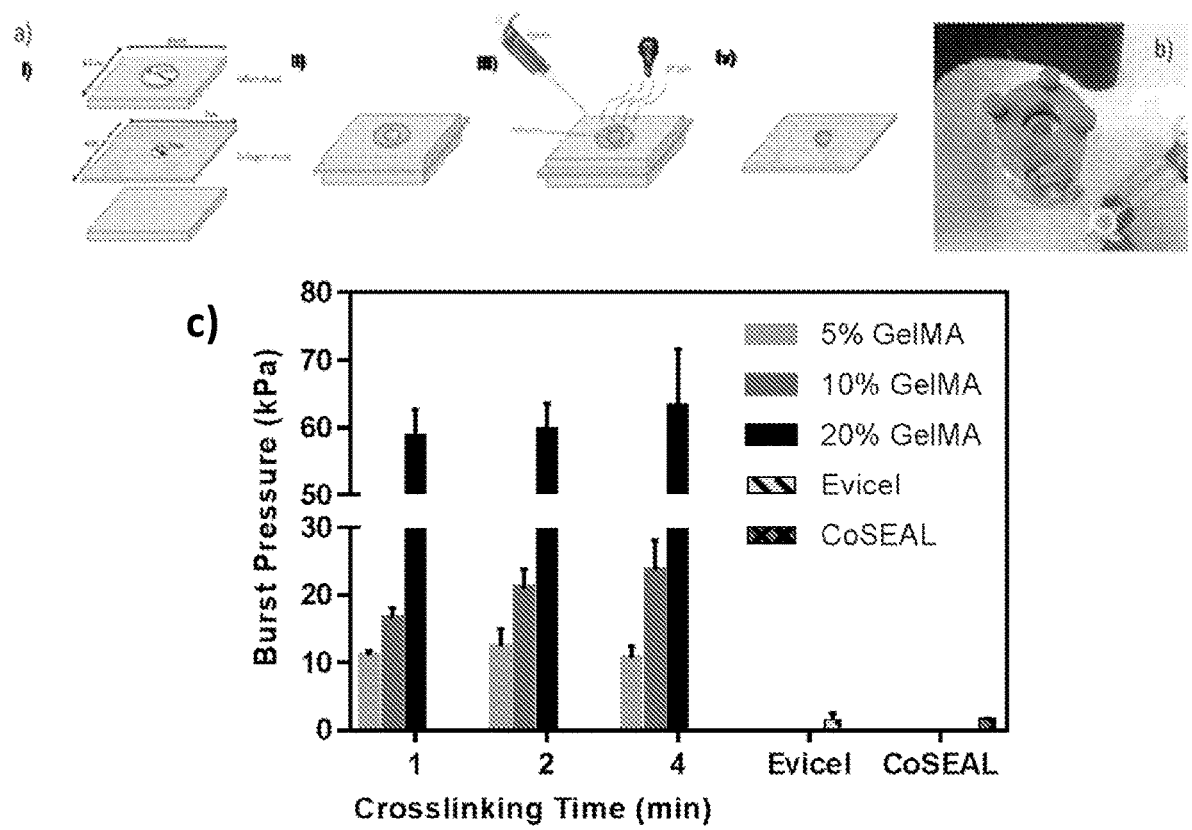
FIG. 7A depicts a schematic of the sample preparation for burst pressure testing.
FIG. 7B shows the top view of the burst pressure test setup (porcine intestine is placed between the metal plates).
FIG. 7C is a bar graph showing burst pressure data for GelMA hydrogel compared to CoSeal and Evicel. GelMA were produced according to Examples 2 and 3.

Example 4: ASTM Standard In Vitro Testing of the Mechanical Properties of Gel-CORE Burst Pressure The burst pressure testing of sealants was adapted from the ASTM standard F2392-04 (standard test method for burst strength of surgical sealants). Porcine skin sheets (40 mm*40 mm) were soaked in PBS prior to sample preparation. A circular defect (3 mm in diameter) was created in the center of a pig skin sheet that was placed between two Teflon sheets (35 mm*35 mm). The top Teflon sheet contained a hole (10 mm in diameter) to allow for application of the desired adhesive over the circular defect in the porcine skin sheet (FIG. 7A). In the case of GelMA, the prepolymer was irradiated with visible light. Afterwards, the collagen sheet was removed and placed into the burst pressure testing system, consisting of pressure detection and recording unit and a syringe pump, which applied air with continuously increasing pressure towards the samples (FIG. 7B). Each tested adhesive group contained five samples.

Increasing air pressure was applied on sealant covering a standardized defect in porcine skin to test the burst pressure resistance. Each GelMA concentration resulted in higher burst pressure values than Coseal™ (FIG. 7C).

Wound Closure

Figures 8A, 8B:
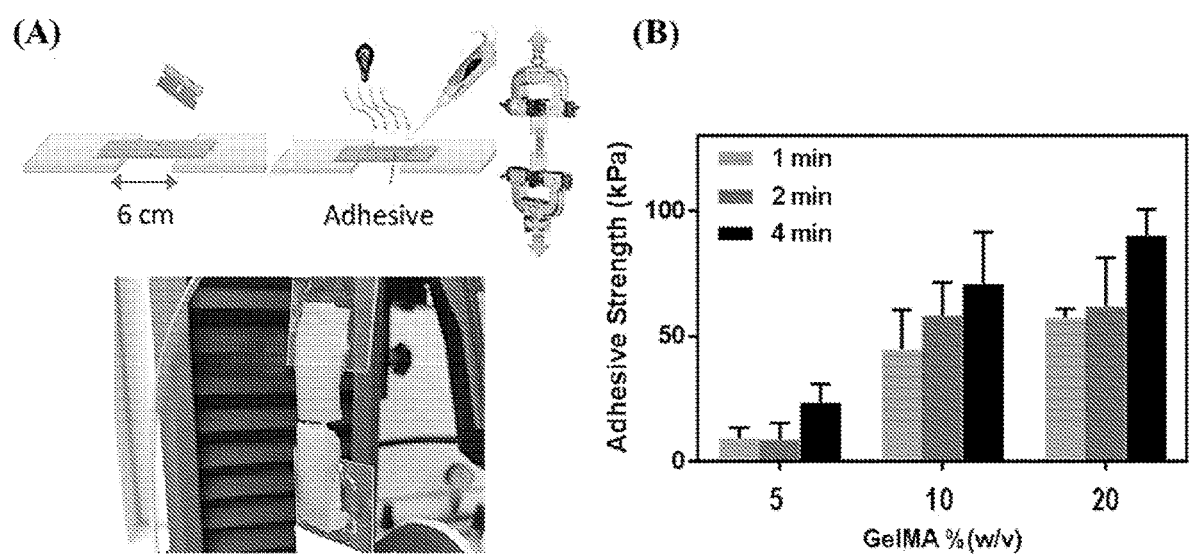
FIG. 8A depicts a schematic of the modified standard test method for wound closure strength (ASTM F2458-05).
FIG. 8B is a bar graph showing adhesive strength of said sealants using the wound closure test at varying GelMA concentrations and exposure times. GelMA were produced according to Examples 2 and 3.

The wound closure strengths of GelMA and the clinically established surgical sealants Evicel® (Ethicon, Somerville, N.J., USA), Coseal™ (Baxter, Deerfield, Ill., USA) and Progel were examined referring to the ASTM standard test F2458-05 (standard test method for wound closure strength of tissue adhesives and sealants), whereas the standard method was slightly modified to fit a smaller sample size. In brief, fresh porcine skin from a local slaughterhouse was prepared by removing the adipose tissue layer and cutting the sample into rectangular sections measuring 5 mm*15 mm. While unused, porcine skin was kept moist in gauze soaked in PBS. Before use, porcine skin was blotted dry to remove excess liquid, and each end of the skin strip was fixed onto two poly(methyl methacrylate) slides (30 mm*60 mm) with Krazy glue (Westerville, Ohio, USA), leaving a 6 mm section of skin between the slides. The porcine skin strip was then cut apart using a razor blade (FIG. 8A), and petroleum jelly was applied with a syringe to the ends of the desired adhesive application area. Afterwards, 40 µl of the adhesive was applied across the 6 mm*5 mm skin section and, in the case of GelMA, irradiated with visible light (FIG. 8A). After 1 hour of incubation in PBS, the two plastic slides were placed into the Instron system grips for tensile testing (FIG. 8A). The adhesive strength of a sealant sample was determined at the point of tearing. Each tested adhesive group contained four to seven samples and results are summarized in FIG. 8B. The tensile test to measured elastic modulus (ranged from 5-50 kPa) and ultimate tensile strength (stress at break point after stretching sample).

Example 5: Degradation and Retention of Gel-CORE

Gel-CORE was applied to a 3-mm >50%-deep corneal defect (10% (w/v) Gel-CORE solution containing 0.01% (w/v) Eosin-Y, 0.5% (w/v) TEA, and 0.5% (w/v) VC was used). The solution was exposed to blue light for 120 seconds to form a hydrogel layer on the damaged cornea.

Figures 9A, 9B, 9C, 9D:
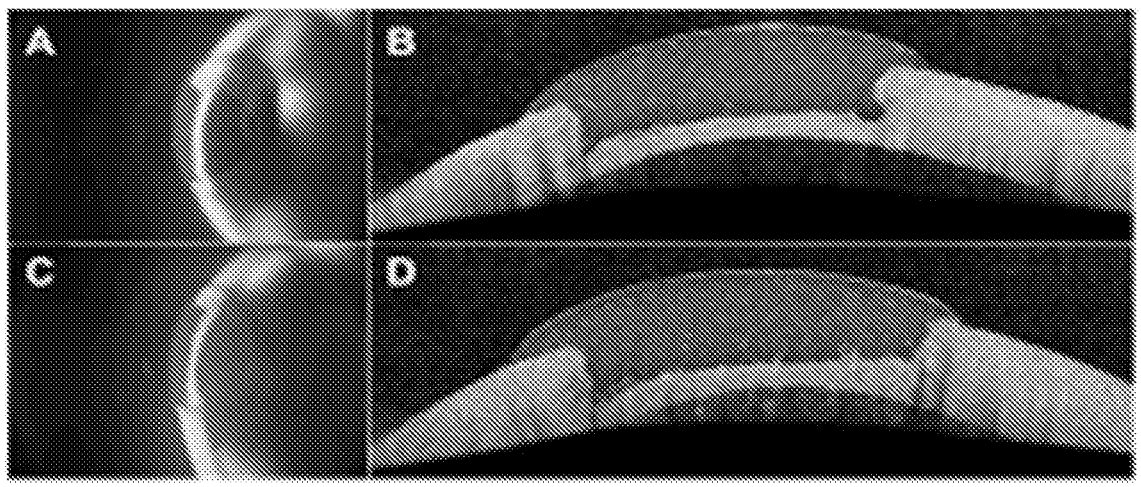
FIGS. 9A-9D show slit lamp photographs (FIGS. 9A and 9C) and OCT images (FIGS. 9B and 9D) immediately after ex vivo application of GelMA to rabbit cornea (FIGS. 9A and 9B) and 11 days later (FIGS. 9C and 9D). As can be seen, there was excellent retention of GelMA.

After the procedure, eyes were kept in PBS at 4° C. Changes in Gel-CORE over time were assessed using serial evaluations with slit lamp biomicroscopy and OCT. It was noted that for at least 11 days, the bioadhesive remained uncompromised (full thickness and spread retained) and stayed completely attached to the cornea in all tested eyes. Slit lamp biomicroscopy showed that during this time, the bioadhesive remained clear with a smooth surface without any biomicroscopic signs of changes in shape or contour (FIGS. 9A and 9C). In addition, OCT confirmed no change in the thickness or shape of Gel-CORE (FIGS. 9B and 9D). After 11 days, the corneal tissue in PBS started to degrade (as expected from necrosis due to prolonged storage in PBS), at which point the Gel-CORE attachment to the cornea began to get compromised.

A corneal injury model in New Zealand white rabbits was used by creating a 50%-deep corneal defect. After general anesthesia of the rabbit using intramuscular injection of ketamine and xylazine, a circular 50%-deep corneal defect was created in the right eye by a 3-mm biopsy punch. Then, a surgical crescent knife was used to perform a lamellar keratectomy. After removing the anterior lamella, the defect surface was dried using a surgical microsponge. Then, 10 µl of the bioadhesive solution was instilled to fill the corneal defect. A microsponge was then used to smooth over the extra solution. This was immediately followed by blue light application (using FocalSeal Xenon Light Source, Genzyme, 100 w/cm$^2$) for 120 seconds to crosslink the bioadhesive. The degradation and retention of Gel-CORE was evaluated using slit lamp biomicroscopy and OCT at 1, 2, and 4 weeks, as described below.

Two outcome measures were evaluated over 4 weeks of follow-up: (i) bioadhesive transparency which measures optical degradation (as evaluated by slit lamp biomicroscopy using Fantes grading scale,[22] which is based on visibility of iris details); and (ii) bioadhesive thickness (as measured by OCT, described below).

Retention is a function of two parameters, degradation and adhesiveness. Either degradation and/or suboptimal adhesiveness can lead to loss of gel retention. To measure retention, OCT technology was used, as described below, to evaluate (i) the presence of the bioadhesive covering the corneal defect; and (ii) the thickness of any gap between the bioadhesive and corneal epithelium or stroma over 4 weeks of follow-up.

Figures 10A, 10B:
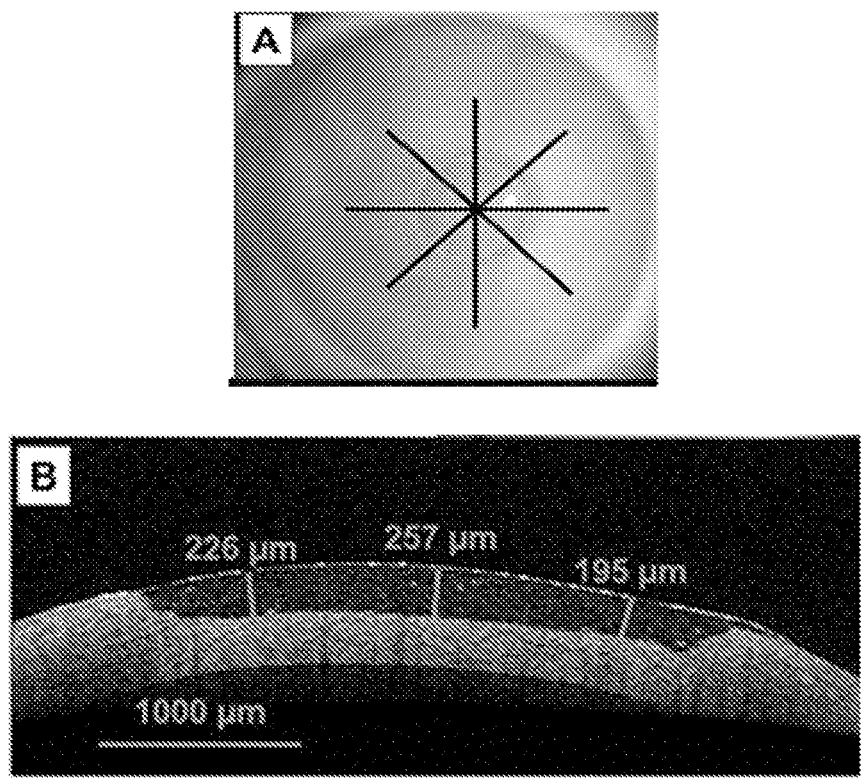
FIG. 10A is a photograph showing line scans obtained at different angles for OCT imaging.
FIG. 10B is an image showing thickness of the bioadhesive which was measured in the center and 1 mm from the center.
Figures 12A, 12B, 12C, 12D, 12E, 12F:
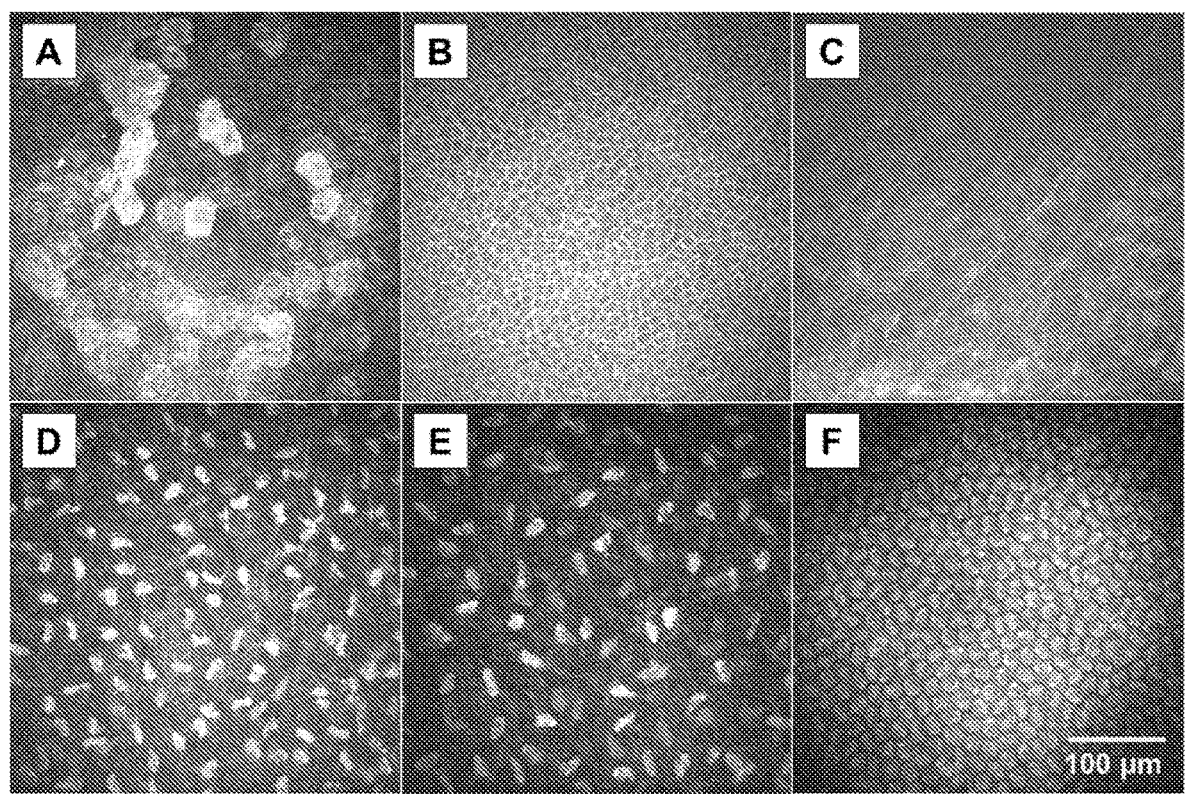
FIGS. 12A-12F are a photographs showing IVCM images of different corneal layers in the rabbit: Superficial epithelium (FIG. 12A), basal epithelium (FIG. 12B), subbasal nerves (FIG. 12C), anterior stromal keratocytes (FIG. 12D), posterior stromal keratocytes (FIG. 12E), and endothelium (FIG. 12F).
Figure 13A:
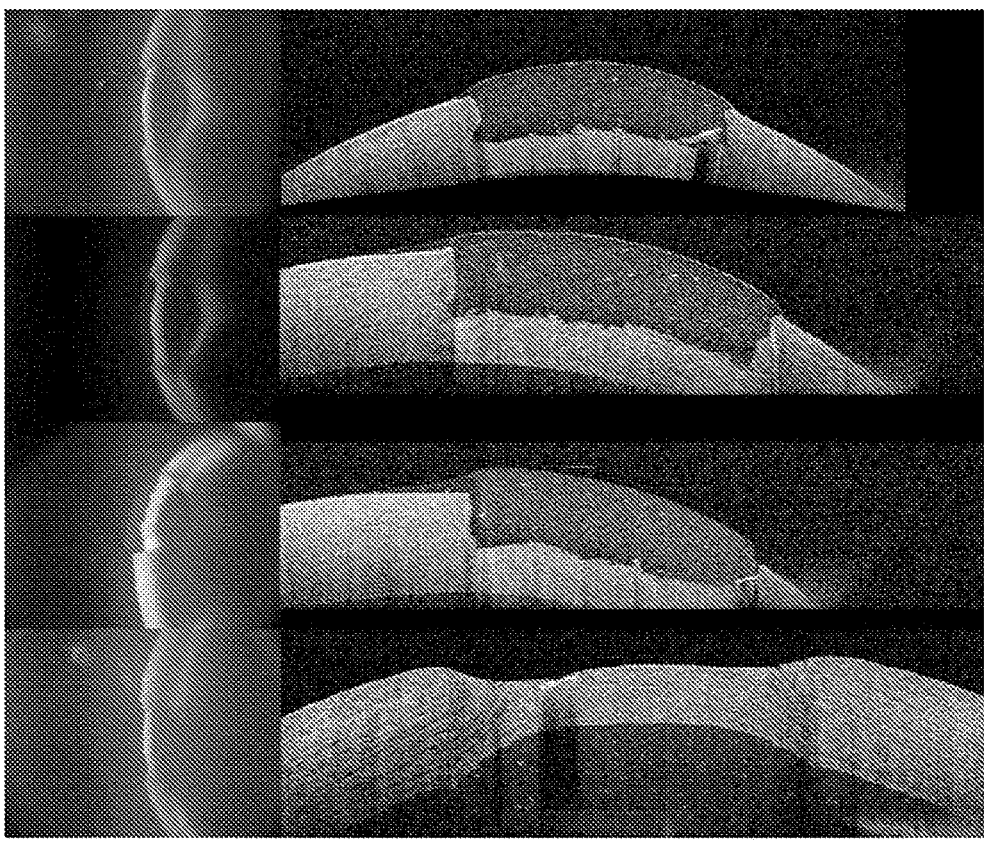
FIGS. 13A-13B are slit lamp photographs and OCT images following GelMA application to partial-thickness corneal defects in two rabbit eyes ex vivo. A 3 mm partial trephination filled with porcine GelMA crosslinked with blue light for 120 seconds.
Figure 13B:
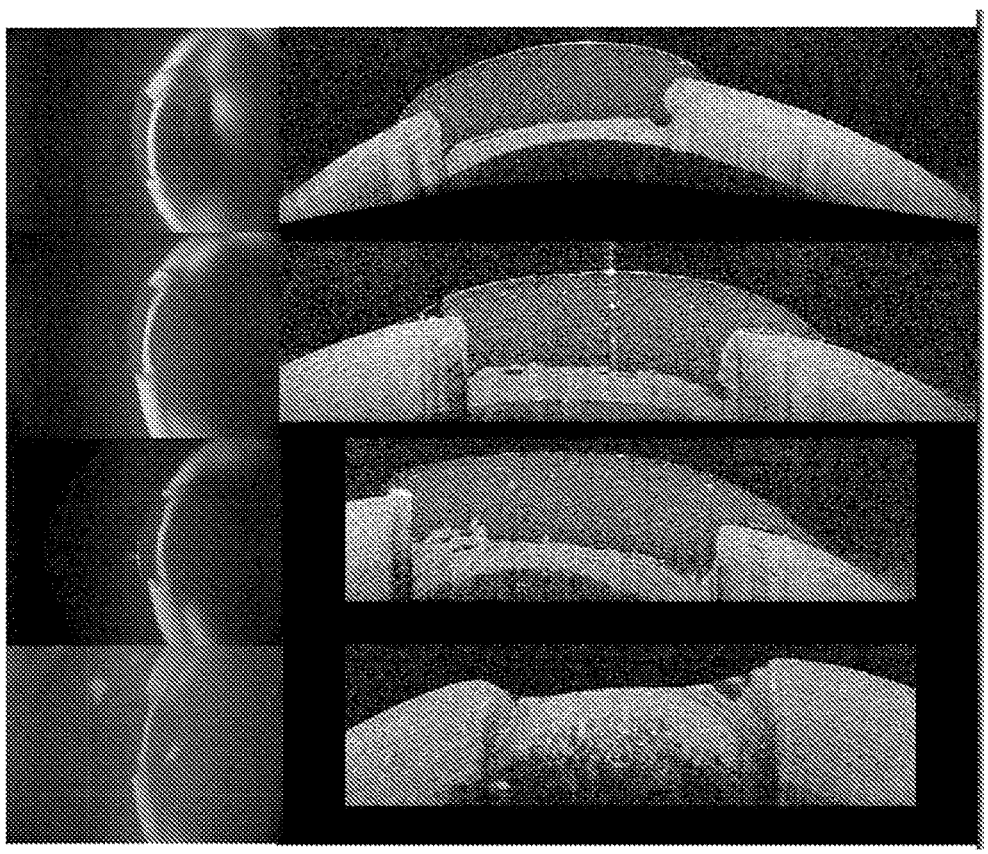
Figures 14A, 14B, 14C:
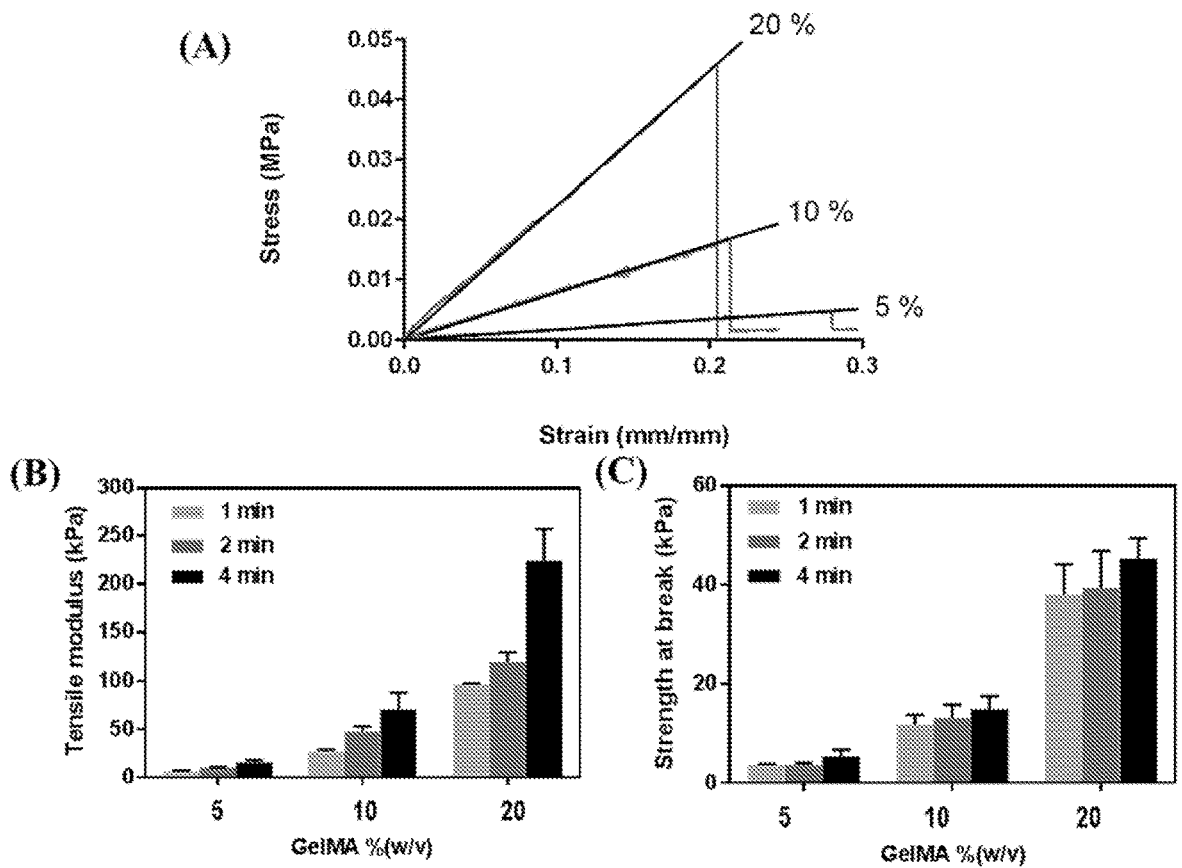
FIGS. 14A-14C show properties of some exemplary GelMA hydrogels of the invention.
Figures 15A, 15B:
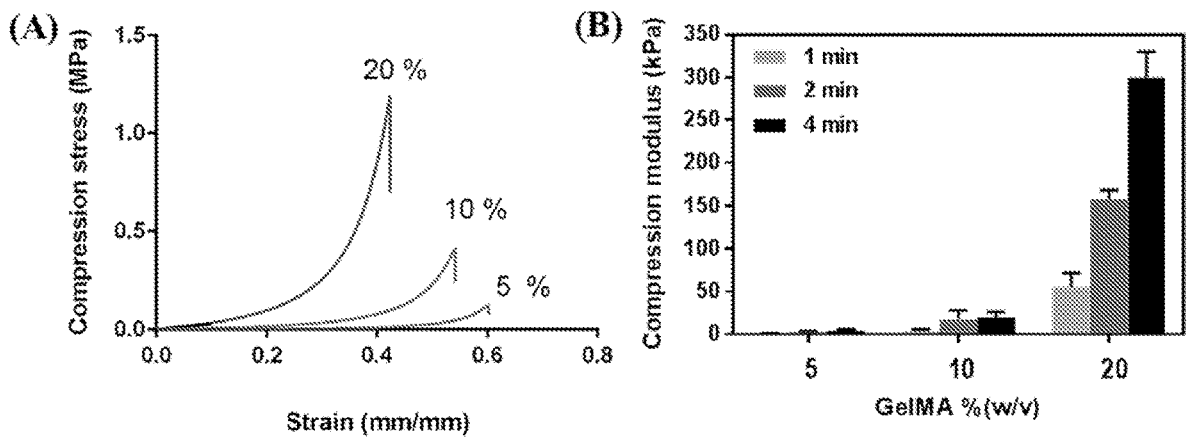
FIGS. 15A-15B show properties of some exemplary GelMA hydrogels of the invention.

Slit lamp biomicroscopy and OCT imaging were performed under general anesthesia for both eyes of the rabbit at 1-week follow-up and subsequently only for the operated eye. For slit lamp examinations, a Topcon Slit Lamp system was used. With a 25× magnification and using slit and broad beams, transparency of the bioadhesive was evaluated (using the Fantes grading scale). Slit lamp photographs were also obtained at the time of examination. Optical Coherence Tomography (OCT) was also employed: this is a non-contact imaging modality that provides high-resolution cross-sectional images of the cornea in vivo. In this experiment, a spectral-domain OCT (Spectralis, Heidelberg Engineering, GmbH, Germany), which has an axial resolution of 3.9-7 µm, was used. Line scans (8 mm long) were performed at 0, 45, 90, and 135 degrees in the central cornea (FIG. 10A). Using the proprietary software of the OCT, the thickness (in microns) of the bioadhesive (in the operated eye) and of the cornea (in the unoperated fellow eye) was measured in the center of the cornea and at 1 mm away from the center in both directions (FIG. 10B). In addition, the thickness of any gap between the bioadhesive and corneal tissue was measured in microns. The slit lamp and OCT findings were compared between the two eyes, and between the different time points to determine the degradation of Gel-CORE and its retention in the corneal defect over time. Based on preliminary data, Gel-CORE can remain intact in vitro for at least 30 days.

Example 6: Biocompatibility and Integration of Gel-CORE

The optimal bioadhesive for cornea repair is not only non-toxic for corneal cells, but also permits cells to integrate into the biomaterial for long-term integration and to prevent extrusion. The in vitro cytocompatibility and integrative capacity of Gel-CORE was determined by using the two most abundant cell types in the cornea including keratocytes and corneal epithelial cells. Keratocytes and corneal epithelial cells were cultured using 2D and 3D culture systems. The biocompatibility and integrative capacity of Gel-CORE was assessed in vivo by investigating the effects of the bioadhesive on corneal cells, as well as the migration of corneal cells into the bioadhesive over time.

In preliminary experiments, the compatibility of Gel-CORE with corneal cells was demonstrated (FIGS. 11A-11G). Corneal keratocytes were incorporated within a representative Gel-CORE composition, showing ≥95% cell survival using 2D culture systems, as well as proliferation and migration of the keratocytes when grown either on top or within the Gel-CORE construct (FIG. 11G).

In Vitro Evaluation of Gel-CORE Cytocompatibility and Cell Integration.

To evaluate the in vitro cytocompatibility of Gel-CORE for the cornea, the following experiments were performed. Corneal cells were cultured in a 5% $CO_2$ humidified incubator at 37° C. in culture media (Dulbecco's Modified Eagle's Medium (DMEM) containing 10% Fetal bovine serum, 1% penicillin-streptomycin, and 1% glutamic acid). A 2D culture system was used in which epithelial cells were seeded on the top of Gel-CORE to form epithelial monolayers. Moreover, a 3D culture system was used to encapsulate the keratocytes inside the Gel-CORE to form cornea tissue.

For 2D culture, Gel-CORE was constructed following exposure to visible light as detailed herein. Then, the gels were seeded with the epithelial cells at cell densities ranging from $1 \times 10^6$ to $1 \times 10^8$ cells/mL and were incubated for 14 days. Media was changed every other day. Cell viability was evaluated on days 1, 4, 7 and 14 by using calcein-AM/ethidium homodimer Live/Dead assays.[23] Actin/DAPI staining was used to assess cellular attachment and spreading as explained previously.[13,24-26] In addition, the metabolic activities of the cells were assessed by using PrestoBlue assay followed by absorbance readings on a microplate spectrophotometer on days 1, 4, 7 and 14. In addition, cellular infiltration and growth within the hydrogels were investigated by histology analyses on day 14.[27-29] Moreover, K12 expression was analyzed for the corneal epithelial cells due to its acclaimed role in maintaining corneal epithelial function. It is critical that epithelial cells grow on the surface of the hydrogel (without penetration into the gel) to form a dense cell layer, which is required for eye protection. Based on these in vitro experiments, Gel-CORE is shown to be non-cytotoxic (cell viability >90%) and promote cellular metabolic activity and adhesion and have limited penetration in the gel.

For 3D culture, keratocytes were mixed with GelMA prepolymer solution at concentrations ranging from $1 \times 10^6$-$1 \times 10^8$ cells/mL. The mixture was then exposed to light to form cell-laden Gel-CORE adhesive. The gels was then washed 3 times with PBS and incubated for 14 days in medium in a culture incubator at 37° C. Cellular viability (Live/Dead assay), cell attachment and spreading (Actin/DAPI), proliferation (Picogreen assay), collagen deposition (Picrosirius Red), and corneal tissue formation (Haematoxylin and eosin staining) was assessed on days 1, 4, 7, and 14. Based on these 3D studies, Gel-CORE was shown to be cytocompatible and will promote cornea tissue formation.

In Vivo Biocompatibility and Integrative Capacity of Gel-CORE in the Cornea.

A Corneal injury model in New Zealand white rabbits was used by creating a 50%-deep corneal defect, as described herein. Rabbits were divided into three groups: (i) Gel-CORE group, in which the bioadhesive was used to fill the corneal defect, as described herein; (ii) Cyanoacrylate group, in which cyanoacrylate glue, which is the standard of care (albeit unapproved) for filling corneal defects to prevent perforation, was used. For this, 10 µl cyanoacrylate glue (MSI-EpiDermGlu+Flex, Medisav Services, Canada) was applied to fill the corneal defect, followed immediately by placement of a soft-bandage contact lens over the cornea. (iii) Control group, in which corneal defect was not filled by any adhesive but received prophylactic antibiotic (erythromycin) ointment for 1 week. The rabbits were then followed for 12 weeks. The biocompatibility and integrative capacity of Gel-CORE and the degree of corneal inflammation and neovascularization were evaluated and compared to other groups using slit lamp biomicroscopy and IVCM (as described below) at 1, 2, 4, and 12 weeks. In addition, at each time point 6 rabbits per group were sacrificed to harvest the cornea for histologic (n=3) and immunohistochemical evaluations (n=3).

For biocompatibility evaluation, the following were considered as the outcome measures: (i) transparency of the cornea surrounding the adhesive/defect (evaluated by slit lamp biomicroscopy using Fantes grading scale); and (ii) density of epithelial cells, stromal keratocytes, inflammatory cells, and blood vessels in the cornea around the bioadhesive (measured by IVCM, histologic staining, and/or immunohistochemical staining, as detailed below).

For evaluation of integrative capacity, the following were considered as the outcome measures: (i) transparency of the bioadhesive (evaluated by slit lamp biomicroscopy using Fantes grading scale); (ii) the extent of migration of corneal epithelial cells over the bioadhesive (measured by slit lamp biomicroscopy, IVCM, and histologic staining, as detailed below), and (iii) density of stromal keratocytes, corneal nerves, inflammatory cells, and blood vessels within the bioadhesive/corneal defect area (measured by IVCM, histologic staining, and/or immunohistochemical staining, described below).

Slit lamp biomicroscopy and IVCM were performed under general anesthesia. As described herein, slit lamp examination and photography were used to assess transparency of the cornea and the bioadhesive. In addition, to assess the migration of epithelium over the bioadhesive, slit lamp photography with fluorescein staining was performed, and the area of corneal epithelial defect over the bioadhesive was measured using ImageJ's Measure Area tool for each time point. In Vivo Confocal Microscopy (IVCM) was employed to evaluate cellular changes and migration in the same rabbits over time without sacrificing the animal. This is a non-invasive imaging modality which provides high-resolution images at the cellular level from the cornea in live animals (FIGS. 12A-12F). In this experiment, a laser scanning IVCM (Heidelberg Retina Tomograph 3 with Rostock Cornea Module, Heidelberg, Germany) was used which utilizes a 670 nm diode laser and has a resolution of 1 µm. It provides images that represent a corneal area of 400×400 µm. For IVCM-based readouts, the following were scaned and examined: (i) the 1.5 mm-central cornea (over the bioadhesive, cyanoacrylate glue, or original defect in the control group); and (ii) the corneal tissue surrounding the 1 mm circumference of the adhesive in 4 quadrants (superior, nasal, inferior, and temporal). For scanning, Sequence Mode was used which automatically acquires 100 consecutive images per sequence. With manual advancing, all corneal layers (epithelium, stroma, and endothelium) were imaged in each scan. Two Sequence Mode scans were obtained in each of five locations (central, superior, nasal, inferior, and temporal). For image analysis in the central cornea, 5 images were randomly selected from different depths in each scan (totally 10 images). For image analysis in the cornea around the adhesive, one randomly selected image from each corneal layer (epithelium, subbasal layer, and stroma) was selected from each individual sequence scan (totally 8 images per layer). For analysis, the density of epithelial cells, subbasal inflammatory cells, and stromal keratocytes were measured by a masked observer using Image J software as previously reported.[30-35] In addition, the density of corneal nerves was also assessed by a masked observer using NeuronJ software as previously reported.[30, 36, 37]

Histologic evaluation using hematoxylin and eosin (H&E) staining was performed on cryosections of the harvested corneas. From each cornea, 5 sections were obtained from the central cornea containing both the defect/adhesive location and the surrounding corneal tissue. For image analysis, all sections were evaluated by a masked observer. Migration of corneal epithelial cells over the adhesive was determined. In addition, the density of stromal keratocytes and inflammatory cells was determined in 10 randomly selected areas within the adhesive (both in the center and periphery of the adhesive) in addition to 10 randomly selected areas of the surrounding cornea at 200 µm from the margin of the adhesive.

Immunohistochemical staining was also performed on cryosections of the harvested cornea with antibodies against the following: β-tubulin III (2G10 Ab; Abcam), beta 2 (CD18) integrin (L13/64 for inflammatory cells; GeneTex), and CD31 (polyclonal anti-CD31 for blood vessels; Abcam). The density of these cells was determined by a masked observer in both the adhesive-applied and surrounding corneal matrix as described for the H&E staining. For this, serial sections from 10 randomly selected areas within the adhesive as well as 10 randomly selected areas of the surrounding cornea within 200 µm of the adhesive were used for analysis. Mean and Standard Deviation (SD) was measured for each metric.

The slit lamp, IVCM, histologic, and immunohistochemical findings were compared between the three groups at each time point to determine the biocompatibility and integrative capacity of Gel-CORE for filling corneal defects. These comparisons between the Gel-CORE group and the control group helped determine whether Gel-CORE caused more or less inflammation and tissue damage than expected from secondary-intention healing (which is also included as a control). In addition, comparisons between the Gel-CORE group and the cyanoacrylate group showed whether the potential tissue damage is less in the Gel-CORE group compared to the current standard of care adhesive. In each group, comparisons between different time points showed whether the integration of corneal cells into Gel-CORE developed over time and whether any potential tissue damage caused by the adhesive subsided or aggravated over time.

Example 7: A New Bioadhesive for Rapid and Long-Term Repair of Corneal Stromal Defects Use of Tunable Properties of Bioadhesive to Optimize its Physical and Adhesive Properties.

The data shows that the GelMA prepolymer with 80-90% degree of methacryloyl functionalization can be effectively crosslinked by using Eosin Y as a photosensitizer, triethanolamine (TEOA) as an initiator, and vinyl caprolactam (VC) as a catalyst to form a stable hydrogel with tunable physical properties. As the crosslinking efficacy is dependent on the concentration of the photosensitizer, initiator, and catalyst, systematic optimization of these conditions is essential. By tuning the concentration of Eosin Y, TEOA, and VC, the critical mechanical properties of the hydrogel can be precisely controlled to derive formulations with tensile and compressive moduli that are comparable to the native cornea (FIGS. 14A-14C, 15A and 15B). Based on the data, optimized concentrations of Eosin Y (0.05 mM), TEOA (0.4% w/v), and VC (0.4% w/v), are used for the following experiments.

Adhesive Properties of Engineered Bioadhesives.

Figures 16A, 16B:
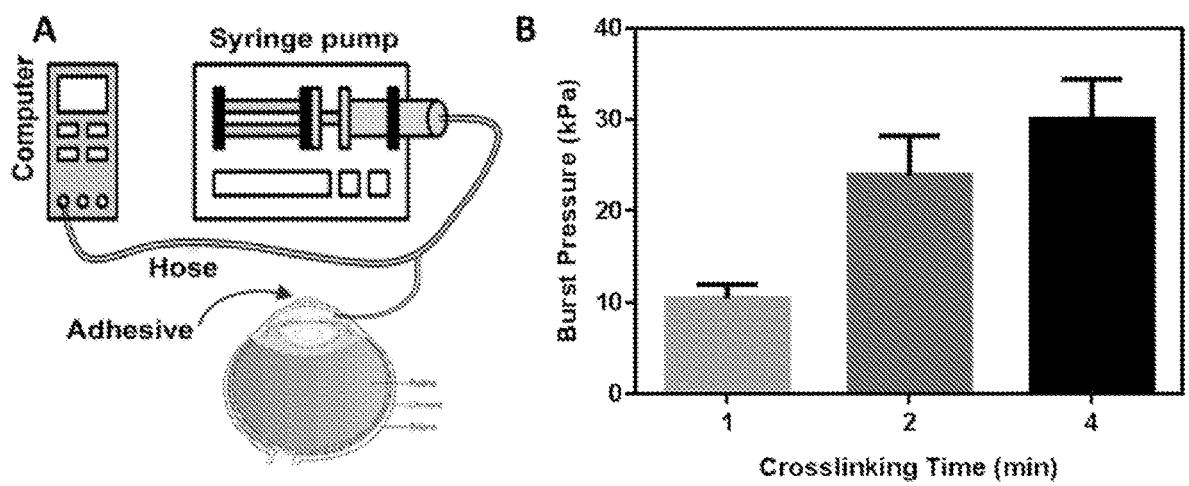
FIGS. 16A-16B show the setup (FIG. 16A) and results (FIG. 16B) for ex vivo burst pressures of cornea sealed by visible light crosslinked GelMA hydrogels formed under varying crosslinking conditions.

A standard burst pressure test was used to obtain a comprehensive estimation of the sealing ability of 20% w/v visible light crosslinked GelMA hydrogels formed at various visible light exposure times. The ex vivo tests were performed to measure the burst pressures of rabbit corneas with 2-mm full-thickness incisions (FIGS. 16A and 16B). The burst pressure of the engineered GelMA was higher than 200 mmHg, almost 10 times the pressure of a healthy eye, and significantly higher than the burst pressure of the commercial control, ReSure® (FIG. 16B).

Ex Vivo Assessment of Smoothness, Transparency, and Retention.

Figure 17:
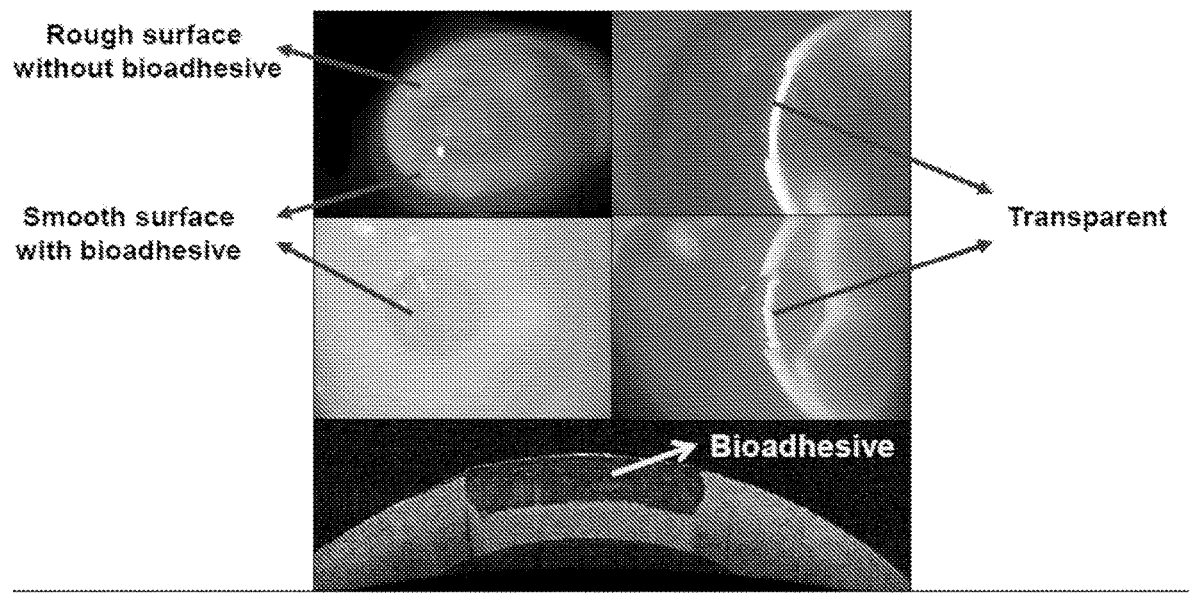
FIG. 17 is a photograph showing ex vivo assessment of smoothness, transparency and retention.

Ex vivo tests were performed using explanted rabbit corneas to assess the GelMA bioadhesives. The bioadhesive was applied ex vivo to a 3-mm >50%-deep corneal defect in New Zealand rabbit eyes. For this, a 20% w/v GelMA solution containing 0.05 mM Eosin-Y, 0.4% w/v TEOA, and 0.4% w/v VC was used. The solution was exposed to visible light for 120 sec to form a hydrogel layer on the corneal defect showing firm adhesion of the bioadhesive to the corneal stroma. In addition, the bioadhesive was transparent with a smooth surface as shown in FIG. 17.

Figure 18:
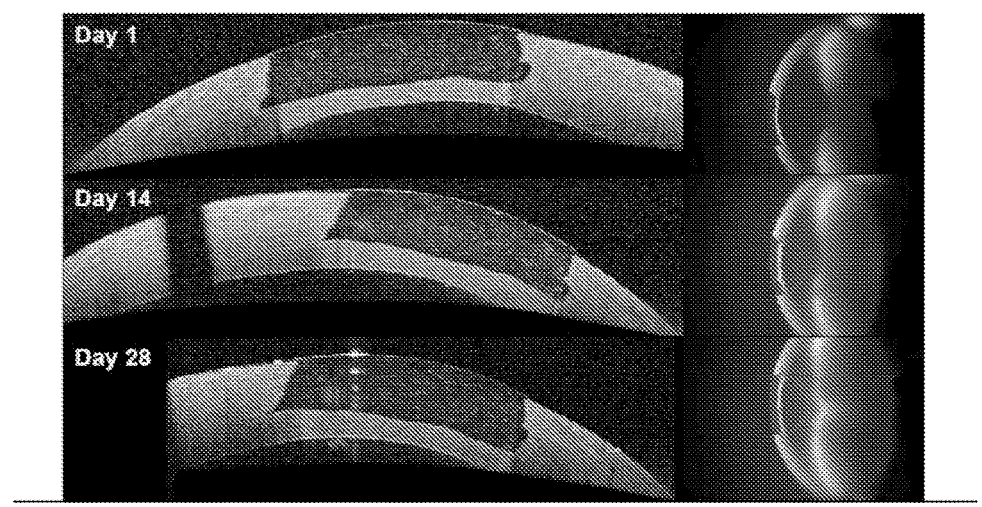
FIG. 18 is a picture showing slit lamp photographs and OCT images immediately after ex vivo application of GEL-CORE to rabbit cornea and 14 and 28 days later showing excellent retention.

After the procedure, the eyes were kept in PBS at 4° C. Changes in the bioadhesive over time were assessed using serial evaluations with slit lamp biomicroscopy and Anterior Segment Optical Coherence Tomography (AS-OCT). It was noted that for the duration of a 30-day assessment period the bioadhesive remained uncompromised (thickness and spread were fully retained) and stayed completely attached to the cornea in all tested eyes. Slit lamp biomicroscopy also showed that during this time the bioadhesive remained clear with a smooth surface without any biomicroscopic signs of changes in shape or contour (FIG. 18). In addition, AS-OCT confirmed no change in the thickness or shape of the bioadhesive.

In Vivo Assessment of Biocompatibility and Biointegration.

A corneal injury model in New Zealand white rabbits was used by creating a 50%-deep corneal defect. After general anesthesia using intramuscular injection of ketamine and xylazine, a central 50%-deep corneal cut was created in the right eye followed by application of the bioadhesive. Immediately after photocrosslinking, there was a firm adhesion of the bioadhesive to the corneal defect. One day after surgery (FIG. 19A-19C), the bioadhesive was transparent with a smooth surface, and the surrounding cornea was transparent and non-inflamed. AS-OCT also showed complete adhesion to the stromal bed. One week after surgery (FIG. 19D-19F), the bioadhesive was still transparent, with some migration of the corneal epithelium over the bioadhesive.

Histologic evaluation of harvested rabbit corneas 2 weeks after undergoing surgery showed migration of epithelial cells over, and migration of keratocytes into, the bioadhesive (FIG. 20C). Additionally, preliminary IHC studies showed a 20.9% decrease in CD45$^+$ cell infiltration in GelMA bioadhesive-filled corneas compared with injured corneas left to heal without bioadhesive.

Example 8: Crosslinking of GelMA Hydrogels $^1$Hnmr Analysis.

Figure 21:
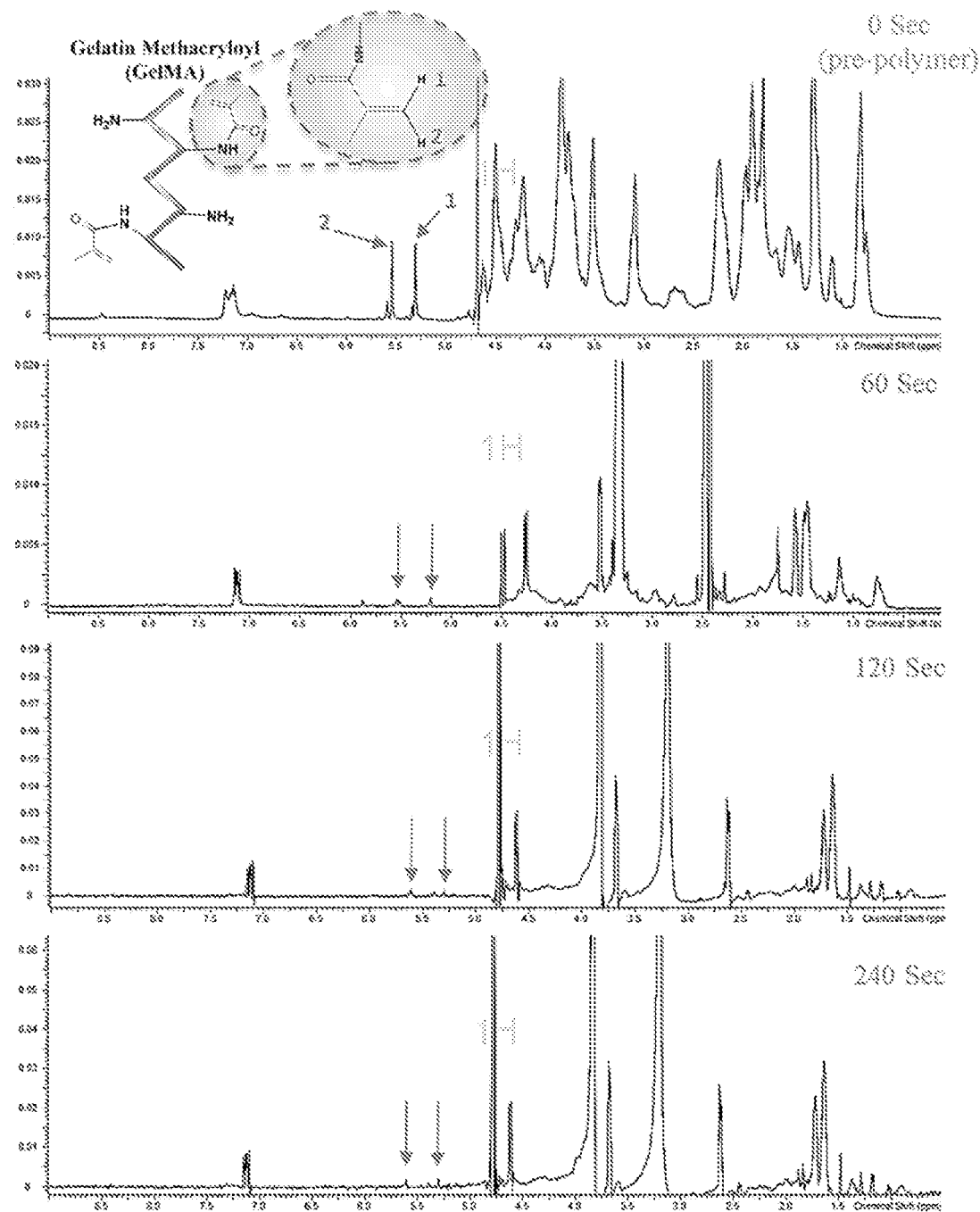
FIG. 21 is a graph showing $^1$HNMR spectrums of GelMA prepolymer and GelMA hydrogels (20% (w/v)) formed at varying visible light exposure times, including 0, 1, 2, and 4 mm.

$^1$H NMR analysis was performed to obtain the crosslinking degree of gelatin methacryloyl (GelMA) hydrogels produced by using various visible light exposure times including 1, 2, and 4 min (FIG. 21). To perform $^1$H NMR test, uncrosslinked GelMA prepolymer and GelMA hydrogels produced at various visible light exposure times were dissolved in deuterated DMSO. In order to quantify the degree of crosslinking, all spectrums were normalized with respect to the phenylalanine signal (δ=6.9-7.3 ppm). It is frequently reported that the signals related to protons of methacrylate groups in GelMA appear at peaks located at δ=5.30 and 5.64 ppm.[47, 48] The degree of crosslinking was calculated as below:

$$\text{Degree of Crosslinking } (DC)\% = \left(1 - \frac{\text{Area(methacrylate groups)}}{\text{Area(phenylalanine signal)}}\right) \times 100$$

which represents the ratio of remaining C=C in the methacrylated groups after the crosslinking process.

$^1$Hnmr Results.

Figure 22:
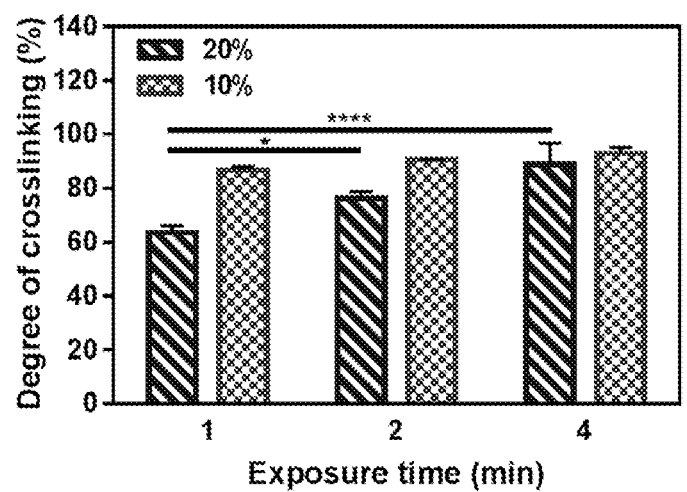
FIG. 22 is a bar graph showing quantification of GelMA hydrogel degree of crosslinking, engineered by using 10 and 20% (w/v) prepolymer concentrations at varying visible light exposure times (1, 2, and 4 min) based on $^1$HNMR spectrums.
Figure 23:
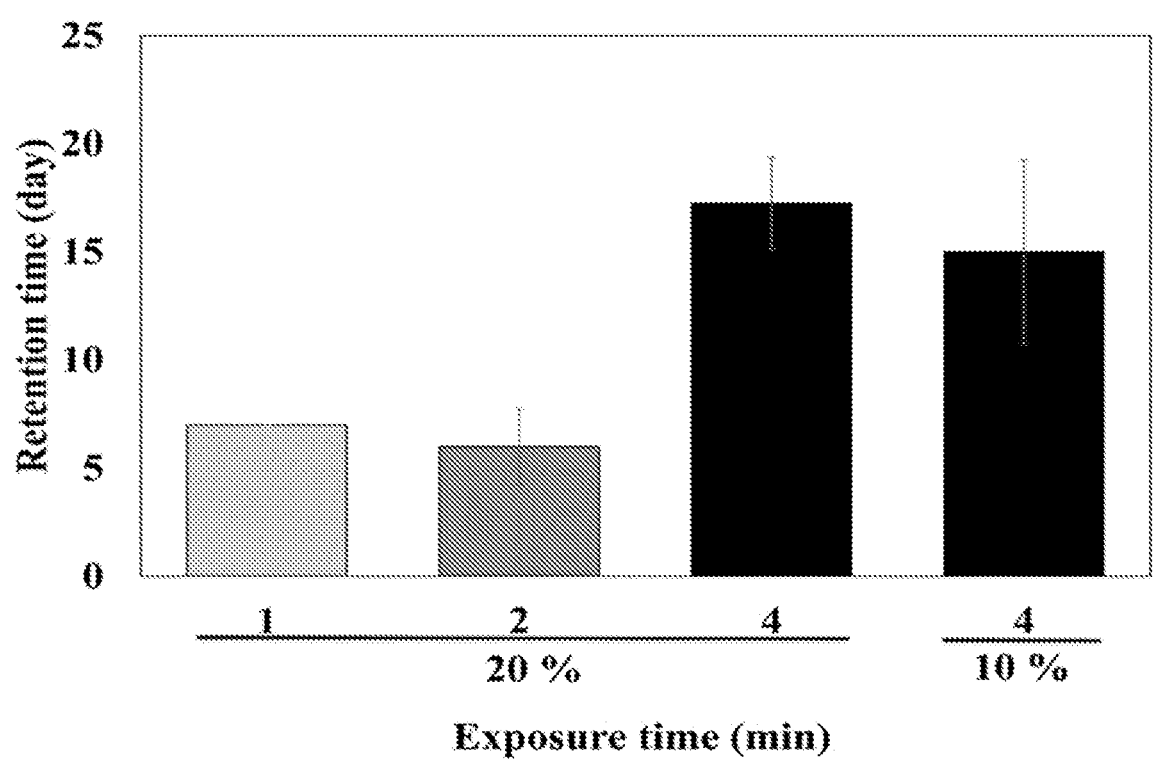
FIG. 23 is a bar graph showing ex vivo retention time of GelMA on explanted rabbit eyes after 18 days of incubation in PBS at 4° C.
Figures 24A, 24B, 24C, 24D:
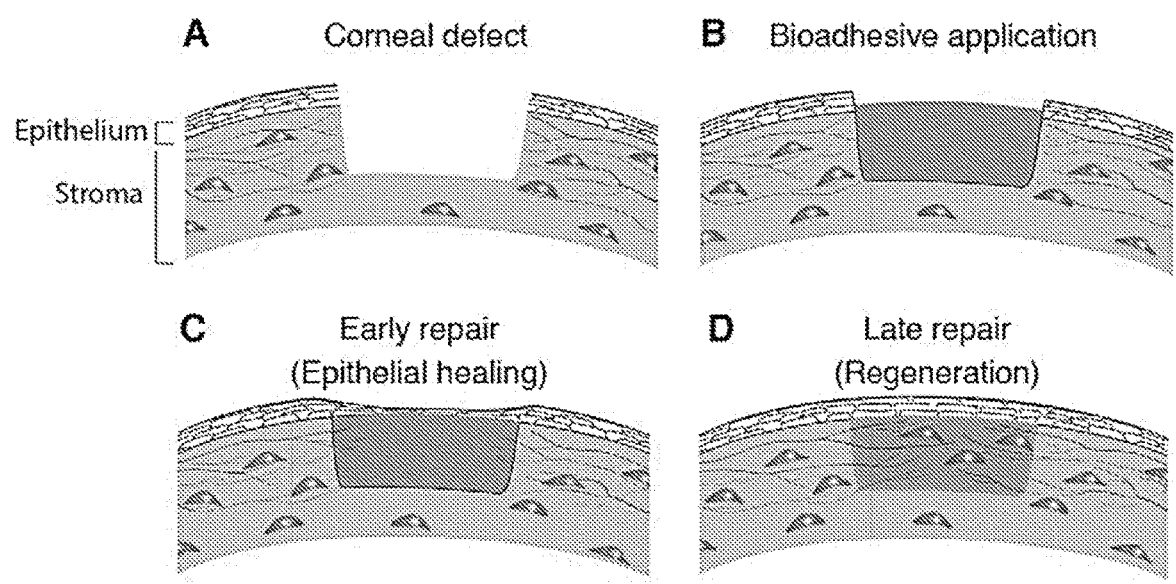
FIGS. 24A-24D show a schematic diagram showing the use of adhesive for rapid and long-term repair of corneal injuries.

Based on $^1$HNMR analysis, the degree of crosslinking was calculated from disappearance of the C=C bond correlated to methacrylated group at δ=5.30 and 5.64 ppm. The degree of crosslinking for 20% (w/v) GelMA hydrogels increased from 63.4±2.7 at 1 min to 88.9±7.8 at 4 min crosslinking time, respectively (FIG. 22 and Table 2). Furthermore, for 10% (w/v) GelMA concentration, after 1 min reaction time, 86.8±1.3 of the original methacrylated groups were consumed (FIG. 22). The degree of crosslinking was 90.7±0.2 and 92.9±2.2% after 2 min and 4 min, respectively.

TABLE 2

Quantification of GelMA hydrogel degree of crosslinking, engineered by using 10% and 20% (w/v) prepolymer concentrations at varying visible light exposure times (1, 2, and 4 min) based on $^1$HNMR spectrums.

| GelMA concentration | Light exposure time (min) | | |
|---|---|---|---|
| % (w/v) | 1 | 2 | 4 |
| 10 | 86.8 ± 1.3 | 90.7 ± 0.2 | 92.9 ± 2.2 |
| 20 | 63.4 ± 2.7 | 76.2 ± 2.4 | 88.9 ± 7.8 |

REFERENCES

Whitcher, J. P., Srinivasan, M. & Upadhyay, M. P Corneal blindness: a global perspective. *Bulletin of the World Health Organization* 79, 214-221 (2001).

Colyer, M. H., Chun, D. W., Bower, K. S., Dick, J. S. & Weichel, E. D. Perforating globe injuries during operation Iraqi Freedom. *Ophthalmology* 115, 2087-2093, doi:10.1016/j.ophtha.2008.05.013 (2008).

3 Thach, A. B. et al. Intraocular foreign body injuries during Operation Iraqi Freedom. *Ophthalmology* 112, 1829-1833, doi:10.1016/j.ophtha.2005.04.024 (2005).

4 www.fda.gov/MedicalDevices/ProductsandMedicalProcedures/DeviceApprovalsandClearances.

5 Weiss, J. L., Williams, P, Lindstrom, R. L. & Doughman, D. J. The use of tissue adhesive in corneal perforations. *Ophthalmology* 90, 610-615 (1983).

Fogle, J. A., Kenyon, K. R. & Foster, C. S. Tissue adhesive arrests stromal melting in the human cornea. *American journal of ophthalmology* 89, 795-802 (1980).

7 Carlson, A. N. & Wilhelmus, K. R. Giant papillary conjunctivitis associated with cyanoacrylate glue. *American journal of ophthalmology* 104, 437-438 (1987).

8 Leahey, A. B., Gottsch, J. D. & Stark, W. J. Clinical experience with N-butyl cyanoacrylate (Nexacryl) tissue adhesive. *Ophthalmology* 100, 173-180 (1993).

9 Hida, T., Sheta, S. M., Proia, A. D. & McCuen, B. W, 2nd. Retinal toxicity of cyanoacrylate tissue adhesive in the rabbit. *Retina* 8, 148-153 (1988).

10 Siegal, J. E. & Zaidman, G. W. Surgical removal of cyanoacrylate adhesive after accidental instillation in the anterior chamber. *Ophthalmic surgery* 20, 179-181 (1989).

11 Papatheofanis, F. J. Prothrombotic cytotoxicity of cyanoacrylate tissue adhesive. *The Journal of surgical research* 47, 309-312 (1989).

12 Cavanaugh, T. B. & Gottsch, J. D. Infectious keratitis and cyanoacrylate adhesive. *American journal of ophthalmology* 111, 466-472 (1991).

13 Annabi, N. et al. Engineered cell-laden human protein-based elastomer. *Biomaterials* 34, 5496-5505, doi:10.1016/j.biomaterials.2013.03.076 (2013).

14 Nichol, J. W. et al. Cell-laden microengineered gelatin methacrylate hydrogels. *Biomaterials* 31, 5536-5544, doi:10.1016/j.biomaterials.2010.03.064 (2010).

15 Nakayama, Y, Kameo, T., Ohtaka, A. & Hirano, Y. Enhancement of visible light-induced gelation of photocurable gelatin by addition of polymeric amine. *Journal of Photochemistry and Photobiology A: Chemistry* 177, 205-211, doi:10.1016/j.jphotochem.2005.05.030 (2006).

16 Orban, J. M., Faucher, K. M., Dluhy, R. A. & Chaikof, E. L. Cytomimetic Biomaterials. 4. In-Situ Photopolymerization of Phospholipids on an Alkylated Surface. *Macromolecules* 33, 4205-4212, doi:10.1021/ma9915780 (2000).

17 Elisseeff, J. et al. Transdermal photopolymerization for minimally invasive implantation. *Proc Natl Acad Sci USA* 96, 3104-3107 (1999).

18 Carnahan, M. A., Middleton, C., Kim, J., Kim, T. & Grinstaff, M. W Hybrid dendritic-linear polyester-ethers for in situ photopolymerization. *J Am Chem Soc* 124, 5291-5293 (2002).

19 Alleyene, C. H., Jr. et al. Efficacy and biocompatibility of a photopolymerized, synthetic, absorbable hydrogel as a dural sealant in a canine craniotomy model. *J Neurosurg* 88, 308-313, doi:10.3171/jns.1998.88.2.0308 (1998).

20 Jun, E. J., Kim, J. H., Purcell, T. L. & Schanzlin, D. J. Comparison of bursting pressure after scleral tunnel incision sealed with sutures or an adherent ocular bandage in human globes. *The Journal of international medical research* 40, 756-760 (2012).

21 Hariprasad, S. M. & Singh, A. Polyethylene glycol hydrogel polymer sealant for vitrectomy surgery: an in vitro study of sutureless vitrectomy incision closure. *Archives of ophthalmology* 129, 322-325, doi:10.1001/archophthalmol.2011.13 (2011).

22 Fantes, F. E. et al. Wound healing after excimer laser keratomileusis (photorefractive keratectomy) in monkeys. *Archives of ophthalmology* 108, 665-675 (1990).

23 Zhao, X. et al. Photocrosslinkable Gelatin Hydrogel for Epidermal Tissue Engineering. *Advanced healthcare materials, doi:*10.1002/adhm.201500005 (2015).

24 Annabi, N. et al. Highly Elastic Micropatterned Hydrogel for Engineering Functional Cardiac Tissue. *Adv Funct Mater* 23, 4950-4959, doi:10.1002/adfm.201300570 (2013).

25 Camci-Unal, G., Cuttica, D., Annabi, N., Demarchi, D. & Khademhosseini, A. Synthesis and characterization of hybrid hyaluronic acid-gelatin hydrogels. *Biomacromolecules* 14, 1085-1092, doi:10.1021/bm3019856 (2013).

26 Camci-Unal, G. et al. Hydrogel surfaces to promote attachment and spreading of endothelial progenitor cells. *Journal of tissue engineering and regenerative medicine* 7, 337-347, doi:10.1002/term.517 (2013).

27 Annabi, N. et al. Synthesis of highly porous crosslinked elastin hydrogels and their interaction with fibroblasts in vitro. *Biomaterials* 30, 4550-4557, doi:10.1016/j.biomaterials.2009.05.014 (2009).

28 Annabi, N., Mithieux, S. M., Weiss, A. S. & Dehghani, F. The fabrication of elastin-based hydrogels using high pressure $CO_2$. *Biomaterials* 30, 1-7 (2009).

29 Annabi, N., Mithieux, S. M., Weiss, A. S. & Dehghani, F. Cross-linked open-pore elastic hydrogels based on tropoelastin, elastin and high pressure $CO_2$. *Biomaterials* 31, 1655-1665, doi:10.1016/j.biomaterials.2009.11.051 (2010).

30 Kheirkhah, A. et al. Effects of corneal nerve density on the response to treatment in dry eye disease. *Ophthalmology* 122, 662-668, doi:10.1016/j.ophtha.2014.11.006 (2015).

31 Kheirkhah, A. et al. Reduced Corneal Endothelial Cell Density in Patients With Dry Eye Disease. *American journal of ophthalmology* 159, 1022-1026 e1022, doi:10.1016/j.ajo.2015.03.011 (2015).

32 Kheirkhah, A., Saboo, U. S., Marmalidou, A. & Dana, R. Overestimation of Corneal Endothelial Cell Density in Smaller Frame Sizes in In Vivo Confocal Microscopy. *Cornea*, doi:10.1097/IC0.0000000000000698 (2015).

33 Kheirkhah, A. et al. Corneal Epithelial Immune Dendritic Cell Alterations in Subtypes of Dry Eye Disease: A Pilot In Vivo Confocal Microscopic Study. *Investigative ophthalmology & visual science* 56, 7179-7185, doi:10.1167/iovs.15-17433 (2015).

34 Patel, D. V. & McGhee, C. N. Quantitative analysis of in vivo confocal microscopy images: a review. *Survey of ophthalmology* 58, 466-475, doi:10.1016/j.survophthal.2012.12.003 (2013).

35 Petroll, W. M. & Robertson, D. M. In Vivo Confocal Microscopy of the Cornea: New Developments in Image Acquisition, Reconstruction, and Analysis Using the HRT-Rostock Corneal Module. *The ocular surface* 13, 187-203, doi:10.1016/j.jtos.2015.05.002 (2015).

36 www.imagescience.org/meijering/software/neuronj/.

37 Kheirkhah, A. et al. Comparison of Standard Versus Wide-Field Composite Images of the Corneal Subbasal Layer by In Vivo Confocal Microscopy. *Investigative ophthalmology & visual science* 56, 5801-5807, doi: 10.1167/iovs.15-17434 (2015).

38 Cha C, Shin S R, Gao X, Annabi N, Dokmeci M R, Tang X S, Khademhosseini A. Controlling mechanical properties of cell-laden hydrogels by covalent incorporation of graphene oxide. Small. 2014 Feb. 12; 10(3):514-23. doi: 10.1002/sml1.201302182. Epub 2013 Oct. 11.

39 Shin S R, Bae H, Cha J M, Mun J Y, Chen Y C, Tekin H, Shin H, Farshchi S, Dokmeci M R, Tang S, Khademhosseini A. Carbon nanotube reinforced hybrid microgels as scaffold materials for cell encapsulation. ACS Nano. 2012 Jan. 24; 6(1):362-72. doi: 10.1021/nn203711s. Epub 2011 Dec. 20.

40 Visser J, Gawlitta D, Benders K E, Toma S M, Pouran B, van Weeren P R, Dhert W J, Malda J. Endochondral bone formation in gelatin methacrylamide hydrogel with embedded cartilage-derived matrix particles. Biomaterials. 2014 Oct. 23; 37C:174-182. doi: 10.1016/j.biomaterials.2014.10.020. [Epub ahead of print]

41 Hjortnaes J, Camci-Unal G, Hutcheson J D, Jung S M, Schoen F J, Kluin J, Aikawa E, Khademhosseini A. Directing Valvular Interstitial Cell Myofibroblast-Like Differentiation in a Hybrid Hydrogel Platform. Adv Healthc Mater. 2014 Jun. 24. doi: 10.1002/adhm.201400029. [Epub ahead of print]

42 Nikkhah M, Eshak N, Zorlutuna P, Annabi N, Castello M, Kim K, Dolatshahi-Pirouz A, Edalat F, Bae H, Yang Y, Khademhosseini A. Directed endothelial cell morphogenesis in micropatterned gelatin methacrylate hydrogels. Biomaterials. 2012 December; 33(35):9009-18. doi: 10.1016/j.biomaterials.2012.08.068. Epub 2012 Sep. 24.

43 Munoz Z, Shih H, Lin C-C. Gelatin hydrogels formed by orthogonal thiol-norbornene photochemistry for cell encapsulation. Biomaterials Science 2014; 2:1063-72.

44 Bernad A, Nieto M A, Vioque A, Palaciáan E. Modification of the amino and hydroxyl groups of lysozyme with carboxylic acid anhydrides: a comparative study. Biochimica et Biophysica Acta (BBA)—Protein Structure and Molecular Enzymology 1986; 873:350-5.

45 Andermann G, Zimmermann G, Schilling E. Application of iron(III)-hydroxamic acid complexes in the spectrophotometric determination of poly(vinyl alcohol) in pharmaceutical preparations. Analyst 1980; 105:575-80.

46 Monzyk B, Crumbliss A L. Mechanism of ligand substitution on high-spin iron(III) by hydroxamic acid chelators. Thermodynamic and kinetic studies on the formation and dissociation of a series of monohydroxamatoiron(III) complexes. Journal of the American Chemical Society 1979; 101:6203-13.

47 Gelatin methacrylate/carboxybetaine methacrylate hydrogels with tunable crosslinking for controlled drug release, J. Mater. Chem. B, 2016, 4, 2304-2313.

48 Biomimetic mineralization of anionic gelatin hydrogels: effect of degree of methacrylation, RSC Adv., 2014, 4, 21997.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A composition for corneal or scleral reconstruction or repair comprising a methacryloyl-substituted gelatin, a visible light activated photoinitiator, and a pharmaceutically acceptable carrier, wherein the methacryloyl-substituted gelatin comprises methacrylamide substitution and methacrylate substitution, and a ratio of methacrylamide substitution to methacrylate substitution in the methacryloyl-substituted gelatin is between 80:20 and 99:1.

2. The composition of claim 1, wherein the methacryloyl-substituted gelatin has a degree of methacryloyl substitution between 30% and 85%.

3. The composition of claim 1, wherein the methacryloyl-substituted gelatin is present at a concentration between 5% and 25% (w/v).

4. The composition of claim 3, wherein the methacryloyl-substituted gelatin is present at a concentration between 8% and 12% (w/v) or between 17% and 23% (w/v).

5. The composition of claim 4, wherein the methacryloyl-substituted gelatin is present at a concentration of about 10% (w/v) or of about 20% (w/v).

6. The composition of claim 1, wherein the visible light activated photoinitiator is selected from the group consisting of: Eosin Y, triethanolamine, vinyl caprolactam, dl-2,3-diketo-1,7,7-trimethylnorcamphane (CQ), 1-phenyl-1,2-propadione (PPD), 2,4,6-trimethylbenzoyl-diphenylphosphine oxide (TPO), bis(2,6-dichlorobenzoyl)-(4-propylphenyl)phosphine oxide (Ir819), 4,4'-bis(dimethylamino)benzophenone, 4,4'-bis(diethylamino) benzophenone, 2-chlorothioxanthen-9-one, 4-(dimethylamino)benzophenone, phenanthrenequinone, ferrocene, diphenyl(2,4,6 trimethylbenzoyl)phosphine oxide/2-hydroxy-2-methylpropiophenone (50/50 blend), dibenzosuberenone, (benzene) tricarbonylchromium, resazurin, resorufin, benzoyltrimethylgermane, and any combination thereof.

7. The composition of claim 1, wherein the visible light activated photoinitiator is a mixture comprising Eosin Y, triethanolamine, and vinyl caprolactam.

8. The composition of claim 7, wherein a concentration of Eosin Y is between 0.0125 and 0.5 mM, a concentration of triethanolamine is between 0.1 and 2% w/v, and a concentration of vinyl caprolactam is between 0.05 and 1.5% w/v.

9. The composition of claim 8, wherein: (i) the concentration of Eosin Y is about 0.1 mM, the concentration of triethanolamine is about 0.5% w/v, and the concentration of vinyl caprolactam is about 0.5% w/v; or (ii) the concentration of Eosin Y is about 0.05 mM, the concentration of triethanolamine is about 0.4% w/v, and the concentration of vinyl caprolactam is about 0.4% w/v.

10. The composition of claim 1, wherein the composition further comprises corneal cells.

11. The composition of claim 1, wherein the composition further comprises a therapeutic agent.

12. A method for corneal or scleral reconstruction or repair, comprising the steps of:
   a. applying a composition of claim 1 to a corneal or scleral defect; and
   b. exposing the composition to visible light.

* * * * *